US008552152B2

(12) United States Patent
Liu

(10) Patent No.: US 8,552,152 B2
(45) Date of Patent: Oct. 8, 2013

(54) COMPOSITIONS AND METHODS FOR MODULATING DOPAMINE NEUROTRANSMISSION

(71) Applicant: Centre for Addiction and Mental Health, Toronto (CA)

(72) Inventor: Fang Liu, Mississauga (CA)

(73) Assignee: Centre for Addiction and Mental Health, Toronto, Ontario (CA)

( * ) Notice: Subject to any disclaimer, the term of this patent is extended or adjusted under 35 U.S.C. 154(b) by 0 days.

(21) Appl. No.: 13/645,780

(22) Filed: Oct. 5, 2012

(65) Prior Publication Data

US 2013/0035293 A1   Feb. 7, 2013

Related U.S. Application Data

(63) Continuation of application No. 12/904,834, filed on Oct. 14, 2010, now Pat. No. 8,304,519, which is a continuation of application No. 11/913,279, filed as application No. PCT/CA2006/007721 on May 5, 2006, now abandoned.

(60) Provisional application No. 60/677,841, filed on May 5, 2005.

(51) Int. Cl.
| C07K 2/00 | (2006.01) |
| C07K 4/00 | (2006.01) |
| C07K 5/00 | (2006.01) |
| C07K 7/00 | (2006.01) |
| C07K 14/00 | (2006.01) |
| A61K 38/00 | (2006.01) |
| A61K 49/00 | (2006.01) |
| A61B 5/00 | (2006.01) |

(52) U.S. Cl.
USPC ............. 530/350; 530/300; 514/1.1; 514/1.2; 424/9.1

(58) Field of Classification Search
None
See application file for complete search history.

(56) References Cited

U.S. PATENT DOCUMENTS

| 5,422,265 A * | 6/1995 | Civelli et al. ............... 435/252.3 |
| 5,580,775 A | 12/1996 | Fremeau et al. ............. 435/325 |
| 5,756,307 A | 5/1998 | Uhl et al. ...................... 435/69.1 |
| 5,885,824 A | 3/1999 | Yamada et al. ............. 435/252.3 |
| 7,348,140 B1 * | 3/2008 | Weiner et al. ................ 435/6.14 |
| 2002/0142299 A1 | 10/2002 | Davidson et al. ................ 435/6 |
| 2003/0186890 A1 | 10/2003 | Drin et al. ........................ 514/14 |
| 2004/0077706 A1 | 4/2004 | Aquila et al. ................. 514/419 |
| 2006/0241082 A1 | 10/2006 | Fleckenstein et al. |

FOREIGN PATENT DOCUMENTS

| CA | 2499601 A1 | 4/2004 |
| EP | 1 376 132 A1 | 1/2004 |
| WO | WO 02/061087 A2 | 8/2002 |
| WO | WO 2004/111636 A2 | 12/2004 |

OTHER PUBLICATIONS

Aarts et al., "Treatment of Ischemic Brain Damage by Perturbing NMDA Receptor-PSD-95 Protein Interactions," Science, 298(5594):846-850 (Oct. 2002).
Banerjee et al., "Pharmacotherapy for Excessive Daytime Sleepiness," Sleep Medicine Reviews, 8(5):339-354 (Oct. 2004).
Berke et al., "Addiction, Dopamine, and the Molecular Mechanisms of Memory," Neuron, 25(3):515-532 (Mar. 2000).
Burgess et al., "Possible Dissociation of the Heparin-binding and Mitogenic Activities of Heparin-binding (Acidic Fibroblast) Growth Factor-1 from Its Receptor-binding Activities by Site-directed Mutagenesis of a Single Lysine Residue," Journal of Cell Biology, 111:2129-2138 (1990).
Bowie et al., "Deciphering the Message in Protein Sequences: Tolerance to Amino Acid Substitutions," Science, 247(4948):1306-1310 (Mar. 16, 1990).
Breier et al., "Schizophrenia is associated with elevated amphetamine-induced synaptic dopamine concentrations: Evidence from a novel positron emission tomography method," Proc. Natl. Acad. Sci. USA, 94(6):2569-2574 (Mar. 1997).
Brown et al., "Treatment of Attention-Deficit/Hyperactivity Disorder: Overview of the Evidence," Pediatrics, 115(6):e749-e757 (Jun. 1, 2005).
Burgess et al., "Possible Dissociation of the Heparin-binding and Mitogenic Activities of Heparin-binding (Acidic Fibroblast) Growth Factor-1 from its Receptor-binding Activities by Site-directed Mutagenesis of a Single Lysine Residue," The Journal of Cell Biology, 111(5 pt.1):2129-2138 (Nov. 1990).
Carneiro et al., "The Multiple LIM Domain-Containing Adaptor Protein Hic-5 Synaptically Colocalizes and Interacts with the Dopamine Transporter," The Journal of Neuroscience, 22(16):7045-7054 (Aug. 15, 2002).
Cass et al., "Direct in vivo evidence that D2 dopamine receptors can modulate dopamine uptake," Neuroscience Letters, 176(2):259-263 (Aug. 1, 1994).
Centonze, et al., "Dopamine D2 Receptor-Mediated Inhibition of Dopaminergic Neurons in Mice Lacking D2L Receptors," Neuropsychopharmacology, 27(5):723-726 (Nov. 2002).
Colman, "Anorectics on Trial: A Half Century of Federal Regulation of Prescription Appetite Suppressants," Annals of Internal Medicine, 143(5):380-385 (Sep. 6, 2005).
Daniels et al., "Regulated Trafficking of the Human Dopamine Transporter," The Journal of Biological Chemistry, 274(50)::35794-35801 (Dec. 10, 1999).
Gainetdinov et al., "Functional Hyperdopaminergia in Dopamine Transporter Knock-Out Mice," Biological Psychiatry, 46(3):303-311 (Aug. 1, 1999).
Girault et al., "The Neurobiology of Dopamine Signaling," Arch. Neurol., 61(5):641-644 (May 2004).

(Continued)

*Primary Examiner* — Chang-Yu Wang
(74) *Attorney, Agent, or Firm* — Winston & Strawn LLP

(57) ABSTRACT

The present invention provides for diagnosis or treatment of neurological or neuropsychiatric disorders involving abnormal dopamine neurotransmission. Methods and agents are provided for modulating dopamine transporter activity and modulating dopaminergic neurotransmission. Agents of the present invention include fragments of D2 receptor or dopamine transporter (DAT) that can disrupt D2-DAT coupling.

8 Claims, 10 Drawing Sheets

(56) References Cited

OTHER PUBLICATIONS

Giros et al., "Hyperlocomotion and indifference to cocaine and amphetamine in mice lacking the dopamine transporter," Nature, 379:606-612 (Feb. 15, 1996).

Hornykiewicz, "Dopamine Miracle: From Brain Homogenate to Dopamine Replacement," Movement Disorders, 17(3):501-508 (May/Jun. 2002).

Jimenez-Jimenez et al., "Therapy in Practice, Pharmacological Options for the Treatment of Tourette's Disorder," Drugs, 61(15):2207-2220 (2001).

Jones et al., "Mechanisms of Amphetamine Action Revealed in Mice Lacking the Dopamine Transporter," the Journal of Neuroscience, 18(6):1979-1986 (Mar. 15, 1998).

Jones et al., "Loss of autoreceptor functions in mice lacking the dopamine transporter", Nature Neuroscience, 2(7):649-655 (Jul. 1999).

Khan et al., "Prominence of the dopamine D2 short isoform in dopaminergic pathways," Proc. Natl. Acad. Sci. USA, 95(13):7731-7736 (Jun. 23, 1998).

Kouzmenko et al., "Intronic Sequences are Involved in Neural Targeting of Human Dopamine Transporter Gene Expression," Biochemical and Biophysical Research Communications, 240:807-811 (1997).

Laruelle et al., "Glutamate, Dopamine, and Schizophrenia From Pathophysiology to Treatment," Ann. N.Y. Acad. Sci., 1003:138-158 (Nov. 2003).

Laruelle et al., "Single photon emission computerized tomography imaging of amphetamine-induced dopamine release in drug-free schizophrenic subjects," Proc. Natl. Acad. Sci. USA, 93(17):9235-9240 (Aug. 20, 1996).

Lee et al., "Syntaxin 1A and Receptor for Activated C Kinase Interact with the N-Terminal Region of Human Dopamine Transporter," Neurochemical Research, 29(7):1405-1409 (Jul. 2004).

Lee et al., "Dual Regulation of NMDA Receptor Functions by Direct Protein-Protein Interactions with the Dopamine D1 Receptor," Cell, 111:219-230 (Oct. 18, 2002).

Lee et al., "Direct binding and functional coupling of α-synuclein to the dopamine transporters accelerate dopamine induced apoptosis," FASEB J., 15(6):916-926 (Apr. 2001).

Lindgren et al., "Distinct roles of dopamine D2L and D2S receptor isoforms in the regulation of protein phosphorylation at presynaptic and postsynaptic sites," Proc. Natl. Acad. Sci. USA, 100(7):4305-4309 (Apr. 1, 2003).

Liu et al., "Direct protein-protein coupling enables cross-talk between opamine D5 and γ-aminobutyric acid A receptors," Nature, 403(6767):274-280 (Jan. 20, 2000).

Lotharius et al., "Pathogenesis of Parkinson's Disease: Dopamine, Vesicles and α-Synuclein," Nature Reviews Neuroscience, 3(12):932-942 (Dec. 2002).

Mayfield et al., "Dopamine $D_2$ Receptor Regulation of the Dopamine Transporter Expressed in *Xenopus laevis* Oocytes is Voltage-Independent," Molecular Pharmacology, 59(1):113-121 (Jan. 2001).

Meiergerd et al., "$D_2$ Receptors May Modulate the Function of the Striatal Transporter for Dopamine: Kinetic Evidence from Studies In Vitro and In Vivo," Journal of Neurochemistry, 61(2):764-767 (Aug. 1993).

Melikian et al., "Membrane Trafficking Regulates the Activity of the Human Dopamine Transporter," The Journal of Neuroscience, 19(18):7699-7710 (Sep. 15, 1999).

Pawson et al., "Assembly of Cell Regulatory Systems through Protein Interaction Domains," Science, 300:445-452 (Apr. 18, 2003).

Raiteri et al., "d-Amphetamine as a Releaser or Reuptake Inhibitor of Biogenic Amines in Synaptosomes," European Journal of Pharmacology, 34(1):189-195 (Nov. 1975).

Ralph et al., "Prepulse Inhibition Deficits and Perseverative Motor Patterns in Dopamine Transporter Knock-Out Mice: Differential Effects of D1 and D2 Receptor Antagonists," The Journal of Neuroscience, 21(1):305-313 (Jan. 1, 2001).

Sacchetti et al., "Characterization of the 5'-flanking region of the human dopamine transporter gene," Molecular Brain Research, 74:167-174 (1999).

Schwarze et al., "In Vivo Protein Transduction: Delivery of a Biologically Active Protein into the Mouse," Science, 285(5433):1569-1572 (Sep. 1999).

Seeman et al., "Antipsychotic Drugs: Direct Correlation between Clinical Potency and Presynaptic Action on Dopamine Neurons," Science, 188(4194):1217-1219 (Jun. 20, 1975).

Sulzer et al., "Amphetamine Redistributes Dopamine from Synaptic Vesicles to the Cytosol and Promotes Reverse Transport," The Journal of Neuroscience, 15(5):4102-4108 (May 1995).

Thase et al., "Remission Rates Following Antidepressant Therapy With Bupropion or Selective Serotonin Reuptake Inhibitors: A Meta-Analysis of Original Data From 7 Randomized Controlled Trials," J. Clin. Psychiatry, 66(8):974-981 (Aug. 2005).

Torres et al., "Functional Interaction between Monoamine Plasma Membrane Transporters and the Synaptic PDZ Domain-Containing Protein PICK1," Neuron, 30:121-134 (Apr. 1, 2001).

Wilson et al., "Striatal Dopamine, Dopamine Transporter, and Vesicular Monoamine Transporter in Chronic Cocaine Users," Annals of Neurology, 40(3):428-439 (Sep. 1996).

Wilson et al., "Striatal dopamine nerve terminal markers in human, chronic methamphetamine users," Nature Medicine, 2(6):699-703 (Jun. 1996).

Wise, "Dopamine, Learning and Motivation," Nature Reviews Neuroscience, 5:483-494 (Jun. 1, 2004).

\* cited by examiner

A

Amino acid

1 ———————————————— 414

Human D2 receptor short isoform (SEQ ID NO:19)

Figure 6A

Human D2 receptor long isoform (SEQ ID NO:20)

Figure 6B

SEQUENCE LISTING

<160> NUMBER OF SEQ ID NOS: 21

<210> SEQ ID NO 1
<211> LENGTH: 34
<212> TYPE: PRT
<213> ORGANISM: Artificial
<220> FEATURE:

```
<223> OTHER INFORMATION: Human D2 dopamine receptor (D2[IL3-2-5]:
      I311-Q344)

<400> SEQUENCE: 1

Ile Phe Glu Ile Gln Thr Met Pro Asn Gly Lys Thr Arg Thr Ser Leu
1               5                   10                  15

Lys Thr Met Ser Arg Arg Lys Leu Ser Gln Gln Lys Glu Lys Lys Ala
            20                  25                  30

Thr Gln

<210> SEQ ID NO 2
<211> LENGTH: 15
<212> TYPE: PRT
<213> ORGANISM: Artificial
<220> FEATURE:
<223> OTHER INFORMATION: Human dopamine transporter protein (DAT[NT1-1]:
      M1-V15)

<400> SEQUENCE: 2

Met Ser Lys Ser Lys Cys Ser Val Gly Leu Met Ser Val Val
1               5                   10              15

<210> SEQ ID NO 3
<211> LENGTH: 103
<212> TYPE: PRT
<213> ORGANISM: Artificial
<220> FEATURE:
<223> OTHER INFORMATION: Human D2 dopamine receptor (D2[IL3-2]:
      E242-Q344)

<400> SEQUENCE: 3

Glu Ala Ala Arg Arg Ala Gln Glu Leu Glu Met Glu Met Leu Ser Ser
1               5                   10                  15

Thr Ser Pro Pro Glu Arg Thr Arg Tyr Ser Pro Ile Pro Pro Ser His
            20                  25                  30

His Gln Leu Thr Leu Pro Asp Pro Ser His His Gly Leu His Ser Thr
        35                  40                  45

Pro Asp Ser Pro Ala Lys Pro Glu Lys Asn Gly His Ala Lys Asp His
50                  55                  60

Pro Lys Ile Ala Lys Ile Phe Glu Ile Gln Thr Met Pro Asn Gly Lys
65                  70                  75                  80

Thr Arg Thr Ser Leu Lys Thr Met Ser Arg Arg Lys Leu Ser Gln Gln
                85                  90                  95

Lys Glu Lys Lys Ala Thr Gln
            100

<210> SEQ ID NO 4
<211> LENGTH: 48
<212> TYPE: PRT
<213> ORGANISM: Artificial
<220> FEATURE:
<223> OTHER INFORMATION: Human D2 dopamine receptor (D2[IL3-2-3]:
      E297-Q344)

<400> SEQUENCE: 4

Glu Lys Asn Gly His Ala Lys Asp His Pro Lys Ile Ala Lys Ile Phe
1               5                   10                  15

Glu Ile Gln Thr Met Pro Asn Gly Lys Thr Arg Thr Ser Leu Lys Thr
            20                  25                  30

Met Ser Arg Arg Lys Leu Ser Gln Gln Lys Glu Lys Lys Ala Thr Gln
        35                  40                  45
```

<210> SEQ ID NO 5
<211> LENGTH: 31
<212> TYPE: PRT
<213> ORGANISM: Artificial
<220> FEATURE:
<223> OTHER INFORMATION: GST linked human dopamine receptor
       (GSTD2[IL3-1]: K211-K241)

<400> SEQUENCE: 5

Lys Ile Tyr Ile Val Leu Arg Arg Arg Arg Lys Arg Val Asn Thr Lys
1               5                   10                  15

Arg Ser Ser Arg Ala Phe Arg Ala His Leu Arg Ala Pro Leu Lys
            20                  25                  30

<210> SEQ ID NO 6
<211> LENGTH: 68
<212> TYPE: PRT
<213> ORGANISM: Artificial
<220> FEATURE:
<223> OTHER INFORMATION: Human dopamine transporter protein (DAT[NT]:
       M1-D68)

<400> SEQUENCE: 6

Met Ser Lys Ser Lys Cys Ser Val Gly Leu Met Ser Ser Val Val Ala
1               5                   10                  15

Pro Ala Lys Glu Pro Asn Ala Val Gly Pro Lys Glu Val Glu Leu Ile
            20                  25                  30

Leu Val Lys Glu Gln Asn Gly Val Gln Leu Thr Ser Ser Thr Leu Thr
        35                  40                  45

Asn Pro Arg Gln Ser Pro Val Glu Ala Gln Asp Arg Glu Thr Trp Gly
    50                  55                  60

Lys Lys Ile Asp
65

<210> SEQ ID NO 7
<211> LENGTH: 26
<212> TYPE: PRT
<213> ORGANISM: Artificial
<220> FEATURE:
<223> OTHER INFORMATION: Human dopamine transporter protein (DAT[NT1]:
       M1-P26)

<400> SEQUENCE: 7

Met Ser Lys Ser Lys Cys Ser Val Gly Leu Met Ser Ser Val Val Ala
1               5                   10                  15

Pro Ala Lys Glu Pro Asn Ala Val Gly Pro
            20                  25

<210> SEQ ID NO 8
<211> LENGTH: 16
<212> TYPE: PRT
<213> ORGANISM: Artificial
<220> FEATURE:
<223> OTHER INFORMATION: GST linked human dopamine receptor (GST-D2[CT]:
       T399-C414)

<400> SEQUENCE: 8

Thr Phe Asn Ile Glu Phe Arg Lys Ala Phe Leu Lys Ile Leu His Cys
1               5                   10                  15

<210> SEQ ID NO 9
<211> LENGTH: 28
<212> TYPE: PRT
<213> ORGANISM: Artificial
<220> FEATURE:
<223> OTHER INFORMATION: Human dopamine transporter protein fragment (NT2: A16-T43)

<400> SEQUENCE: 9

Ala Pro Ala Lys Glu Pro Asn Ala Val Gly Pro Lys Glu Val Glu Leu
1               5                   10                  15

Ile Leu Val Lys Glu Gln Asn Gly Val Gln Leu Thr
            20                  25

<210> SEQ ID NO 10
<211> LENGTH: 34
<212> TYPE: PRT
<213> ORGANISM: Artificial
<220> FEATURE:
<223> OTHER INFORMATION: Human dopamine transportr protein fragment
      (NT3: K35-D68)

<400> SEQUENCE: 10

Lys Glu Gln Asn Gly Val Gln Leu Thr Ser Ser Thr Leu Thr Asn Pro
1               5                   10                  15

Arg Gln Ser Pro Val Glu Ala Gln Asp Arg Glu Thr Trp Gly Lys Lys
            20                  25                  30

Ile Asp

<210> SEQ ID NO 11
<211> LENGTH: 11
<212> TYPE: PRT
<213> ORGANISM: Artificial
<220> FEATURE:
<223> OTHER INFORMATION: Human dopamine transporter protein fragment
      (NT1-2: A16-P26)

<400> SEQUENCE: 11

Ala Pro Ala Lys Glu Pro Asn Ala Val Gly Pro
1               5                   10

<210> SEQ ID NO 12
<211> LENGTH: 26
<212> TYPE: PRT
<213> ORGANISM: Artificial
<220> FEATURE:
<223> OTHER INFORMATION: HIV virus type 1 TAT protein fused to human
      dopamine transporter protein (TAT-DAT[NT1-1])

<400> SEQUENCE: 12

Tyr Gly Arg Lys Lys Arg Arg Gln Arg Arg Met Ser Lys Ser Lys
1               5                   10                  15

Cys Ser Val Gly Leu Met Ser Ser Val Val
            20                  25

<210> SEQ ID NO 13
<211> LENGTH: 22
<212> TYPE: PRT
<213> ORGANISM: Artificial
<220> FEATURE:
<223> OTHER INFORMATION: HIV virus type 1 TAT protein fused to human
      dopamine transporter protein (TAT-DAT[NT1-2])

<400> SEQUENCE: 13

Tyr Gly Arg Lys Lys Arg Arg Gln Arg Arg Ala Pro Ala Lys Glu
1               5                   10                  15

Pro Asn Ala Val Gly Pro
            20

<210> SEQ ID NO 14
<211> LENGTH: 11

```
<212> TYPE: PRT
<213> ORGANISM: Artificial
<220> FEATURE:
<223> OTHER INFORMATION: HIV virus type 1 TAT protein

<400> SEQUENCE: 14

Tyr Gly Arg Lys Lys Arg Arg Gln Arg Arg Arg
1               5                   10

<210> SEQ ID NO 15
<211> LENGTH: 30
<212> TYPE: PRT
<213> ORGANISM: Artificial
<220> FEATURE:
<223> OTHER INFORMATION: Human D2 dopamine receptor (D2[IL3-2-1]:
      E242-P271)

<400> SEQUENCE: 15

Glu Ala Ala Arg Arg Ala Gln Glu Leu Glu Met Glu Met Leu Ser Ser
1               5                   10                  15

Thr Ser Pro Pro Glu Arg Thr Arg Tyr Ser Pro Ile Pro Pro
            20                  25                  30

<210> SEQ ID NO 16
<211> LENGTH: 53
<212> TYPE: PRT
<213> ORGANISM: Artificial
<220> FEATURE:
<223> OTHER INFORMATION: Human D2 dopamine receptor (D2[IL3-2-2]:
      S259-I311)

<400> SEQUENCE: 16

Ser Pro Pro Glu Arg Thr Arg Tyr Ser Pro Ile Pro Pro Ser His His
1               5                   10                  15

Gln Leu Thr Leu Pro Asp Pro Ser His His Gly Leu His Ser Thr Pro
            20                  25                  30

Asp Ser Pro Ala Lys Pro Glu Lys Asn Gly His Ala Lys Asp His Pro
        35                  40                  45

Lys Ile Ala Lys Ile
    50

<210> SEQ ID NO 17
<211> LENGTH: 15
<212> TYPE: PRT
<213> ORGANISM: Artificial
<220> FEATURE:
<223> OTHER INFORMATION: Human D2 dopamine receptor (D2[IL3-2-4]
      (E297-I311))

<400> SEQUENCE: 17

Glu Lys Asn Gly His Ala Lys Asp His Pro Lys Ile Ala Lys Ile
1               5                   10                  15

<210> SEQ ID NO 18
<211> LENGTH: 38
<212> TYPE: PRT
<213> ORGANISM: Artificial
<220> FEATURE:
<223> OTHER INFORMATION: Human dopamine transporter protein
      (DAT[CT]:L583-V620)

<400> SEQUENCE: 18

Leu Pro Gly Ser Phe Arg Glu Lys Leu Ala Tyr Ala Ile Ala Pro Glu
1               5                   10                  15

Lys Asp Arg Glu Leu Val Asp Arg Gly Glu Val Arg Gln Phe Thr Leu
            20                  25                  30
```

Arg His Trp Leu Lys Val
        35

<210> SEQ ID NO 19
<211> LENGTH: 414
<212> TYPE: PRT
<213> ORGANISM: Artificial
<220> FEATURE:
<223> OTHER INFORMATION: human D2 receptor short isoform

<400> SEQUENCE: 19

Met Asp Pro Leu Asn Leu Ser Trp Tyr Asp Asp Leu Glu Arg Gln
1               5                   10                  15

Asn Trp Ser Arg Pro Phe Asn Gly Ser Asp Gly Lys Ala Asp Arg Pro
            20                  25                  30

His Tyr Asn Tyr Tyr Ala Thr Leu Leu Thr Leu Leu Ile Ala Val Ile
            35                  40                  45

Val Phe Gly Asn Val Leu Val Cys Met Ala Val Ser Arg Glu Lys Ala
        50                  55                  60

Leu Gln Thr Thr Thr Asn Tyr Leu Ile Val Ser Leu Ala Val Ala Asp
65                  70                  75                  80

Leu Leu Val Ala Thr Leu Val Met Pro Trp Val Val Tyr Leu Glu Val
                85                  90                  95

Val Gly Glu Trp Lys Phe Ser Arg Ile His Cys Asp Ile Phe Val Thr
            100                 105                 110

Leu Asp Val Met Met Cys Thr Ala Ser Ile Leu Asn Leu Cys Ala Ile
            115                 120                 125

Ser Ile Asp Arg Tyr Thr Ala Val Ala Met Pro Met Leu Tyr Asn Thr
        130                 135                 140

Arg Tyr Ser Ser Lys Arg Arg Val Thr Val Met Ile Ser Ile Val Trp
145                 150                 155                 160

Val Leu Ser Phe Thr Ile Ser Cys Pro Leu Leu Phe Gly Leu Asn Asn
                165                 170                 175

Ala Asp Gln Asn Glu Cys Ile Ile Ala Asn Pro Ala Phe Val Val Tyr
            180                 185                 190

Ser Ser Ile Val Ser Phe Tyr Val Pro Phe Ile Val Thr Leu Leu Val
        195                 200                 205

Tyr Ile Lys Ile Tyr Ile Val Leu Arg Arg Arg Arg Lys Arg Val Asn
        210                 215                 220

Thr Lys Arg Ser Ser Arg Ala Phe Arg Ala His Leu Arg Ala Pro Leu
225                 230                 235                 240

Lys Glu Ala Ala Arg Arg Ala Gln Glu Leu Glu Met Glu Met Leu Ser
                245                 250                 255

Ser Thr Ser Pro Pro Glu Arg Thr Arg Tyr Ser Pro Ile Pro Pro Ser
            260                 265                 270

His His Gln Leu Thr Leu Pro Asp Pro Ser His His Gly Leu His Ser
        275                 280                 285

Thr Pro Asp Ser Pro Ala Lys Pro Glu Lys Asn Gly His Ala Lys Asp
        290                 295                 300

His Pro Lys Ile Ala Lys Ile Phe Glu Ile Gln Thr Met Pro Asn Gly
305                 310                 315                 320

Lys Thr Arg Thr Ser Leu Lys Thr Met Ser Arg Arg Lys Leu Ser Gln
                325                 330                 335

Gln Lys Glu Lys Lys Ala Thr Gln Met Leu Ala Ile Val Leu Gly Val
            340                 345                 350

```
Phe Ile Ile Cys Trp Leu Pro Phe Phe Ile Thr His Ile Leu Asn Ile
            355                 360                 365
His Cys Asp Cys Asn Ile Pro Pro Val Leu Tyr Ser Ala Phe Thr Trp
        370                 375                 380
Leu Gly Tyr Val Asn Ser Ala Val Asn Pro Ile Ile Tyr Thr Thr Phe
385                 390                 395                 400
Asn Ile Glu Phe Arg Lys Ala Phe Leu Lys Ile Leu His Cys
                405                 410
```

<210> SEQ ID NO 20
<211> LENGTH: 443
<212> TYPE: PRT
<213> ORGANISM: Artificial
<220> FEATURE:
<223> OTHER INFORMATION: human D2 receptor long isoform

<400> SEQUENCE: 20

```
Met Asp Pro Leu Asn Leu Ser Trp Tyr Asp Asp Leu Glu Arg Gln
1               5                   10                  15
Asn Trp Ser Arg Pro Phe Asn Gly Ser Asp Gly Lys Ala Asp Arg Pro
                20                  25                  30
His Tyr Asn Tyr Tyr Ala Thr Leu Leu Thr Leu Leu Ile Ala Val Ile
            35                  40                  45
Val Phe Gly Asn Val Leu Val Cys Met Ala Val Ser Arg Glu Lys Ala
    50                  55                  60
Leu Gln Thr Thr Thr Asn Tyr Leu Ile Val Ser Leu Ala Val Ala Asp
65                  70                  75                  80
Leu Leu Val Ala Thr Leu Val Met Pro Trp Val Val Tyr Leu Glu Val
                85                  90                  95
Val Gly Glu Trp Lys Phe Ser Arg Ile His Cys Asp Ile Phe Val Thr
            100                 105                 110
Leu Asp Val Met Met Cys Thr Ala Ser Ile Leu Asn Leu Cys Ala Ile
        115                 120                 125
Ser Ile Asp Arg Tyr Thr Ala Val Ala Met Pro Met Leu Tyr Asn Thr
    130                 135                 140
Arg Tyr Ser Ser Lys Arg Arg Val Thr Val Met Ile Ser Ile Val Trp
145                 150                 155                 160
Val Leu Ser Phe Thr Ile Ser Cys Pro Leu Leu Phe Gly Leu Asn Asn
                165                 170                 175
Ala Asp Gln Asn Glu Cys Ile Ile Ala Asn Pro Ala Phe Val Val Tyr
            180                 185                 190
Ser Ser Ile Val Ser Phe Tyr Val Pro Phe Ile Val Thr Leu Leu Val
        195                 200                 205
Tyr Ile Lys Ile Tyr Ile Val Leu Arg Arg Arg Arg Lys Arg Val Asn
    210                 215                 220
Thr Lys Arg Ser Ser Arg Ala Phe Arg Ala His Leu Arg Ala Pro Leu
225                 230                 235                 240
Lys Gly Asn Cys Thr His Pro Glu Asp Met Lys Leu Cys Thr Val Ile
                245                 250                 255
Met Lys Ser Asn Gly Ser Phe Pro Val Asn Arg Arg Arg Val Glu Ala
            260                 265                 270
Ala Arg Arg Ala Gln Glu Leu Glu Met Glu Met Leu Ser Ser Thr Ser
        275                 280                 285
Pro Pro Glu Arg Thr Arg Tyr Ser Pro Ile Pro Pro Ser His His Gln
    290                 295                 300
Leu Thr Leu Pro Asp Pro Ser His His Gly Leu His Ser Thr Pro Asp
```

```
            305                 310                 315                 320
Ser Pro Ala Lys Pro Glu Lys Asn Gly His Ala Lys Asp His Pro Lys
                325                 330                 335

Ile Ala Lys Ile Phe Glu Ile Gln Thr Met Pro Asn Gly Lys Thr Arg
                340                 345                 350

Thr Ser Leu Lys Thr Met Ser Arg Arg Lys Leu Ser Gln Gln Lys Glu
                355                 360                 365

Lys Lys Ala Thr Gln Met Leu Ala Ile Val Leu Gly Val Phe Ile Ile
            370                 375                 380

Cys Trp Leu Pro Phe Phe Ile Thr His Ile Leu Asn Ile His Cys Asp
385                 390                 395                 400

Cys Asn Ile Pro Pro Val Leu Tyr Ser Ala Phe Thr Trp Leu Gly Tyr
                405                 410                 415

Val Asn Ser Ala Val Asn Pro Ile Ile Tyr Thr Thr Phe Asn Ile Glu
                420                 425                 430

Phe Arg Lys Ala Phe Leu Lys Ile Leu His Cys
                435                 440

<210> SEQ ID NO 21
<211> LENGTH: 620
<212> TYPE: PRT
<213> ORGANISM: Artificial
<220> FEATURE:
<223> OTHER INFORMATION: Human dopamine transporter protein

<400> SEQUENCE: 21

Met Ser Lys Ser Lys Cys Ser Val Gly Leu Met Ser Ser Val Val Ala
1               5                   10                  15

Pro Ala Lys Glu Pro Asn Ala Val Gly Pro Lys Glu Val Glu Leu Ile
                20                  25                  30

Leu Val Lys Glu Gln Asn Gly Val Gln Leu Thr Ser Ser Thr Leu Thr
            35                  40                  45

Asn Pro Arg Gln Ser Pro Val Glu Ala Gln Asp Arg Glu Thr Trp Gly
    50                  55                  60

Lys Lys Ile Asp Phe Leu Leu Ser Val Ile Gly Phe Ala Val Asp Leu
65                  70                  75                  80

Ala Asn Val Trp Arg Phe Pro Tyr Leu Cys Tyr Lys Asn Gly Gly Gly
                85                  90                  95

Ala Phe Leu Val Pro Tyr Leu Leu Phe Met Val Ile Ala Gly Met Pro
                100                 105                 110

Leu Phe Tyr Met Glu Leu Ala Leu Gly Gln Phe Asn Arg Glu Gly Ala
            115                 120                 125

Ala Gly Val Trp Lys Ile Cys Pro Ile Leu Lys Gly Val Gly Phe Thr
        130                 135                 140

Val Ile Leu Ile Ser Leu Tyr Val Gly Phe Phe Tyr Asn Val Ile Ile
145                 150                 155                 160

Ala Trp Ala Leu His Tyr Leu Phe Ser Ser Phe Thr Thr Glu Leu Pro
                165                 170                 175

Trp Ile His Cys Asn Asn Ser Trp Asn Ser Pro Asn Cys Ser Asp Ala
                180                 185                 190

His Pro Gly Asp Ser Ser Gly Asp Ser Ser Gly Leu Asn Asp Thr Phe
            195                 200                 205

Gly Thr Thr Pro Ala Ala Glu Tyr Phe Glu Arg Gly Val Leu His Leu
        210                 215                 220

His Gln Ser His Gly Ile Asp Asp Leu Gly Pro Pro Arg Trp Gln Leu
225                 230                 235                 240
```

-continued

```
Thr Ala Cys Leu Val Leu Val Ile Val Leu Leu Tyr Phe Ser Leu Trp
            245                 250                 255
Lys Gly Val Lys Thr Ser Gly Lys Val Val Trp Ile Thr Ala Thr Met
        260                 265                 270
Pro Tyr Val Val Leu Thr Ala Leu Leu Leu Arg Gly Val Thr Leu Pro
            275                 280                 285
Gly Ala Ile Asp Gly Ile Arg Ala Tyr Leu Ser Val Asp Phe Tyr Arg
        290                 295                 300
Leu Cys Glu Ala Ser Val Trp Ile Asp Ala Ala Thr Gln Val Cys Phe
305                 310                 315                 320
Ser Leu Gly Val Gly Phe Gly Val Leu Ile Ala Phe Ser Ser Tyr Asn
            325                 330                 335
Lys Phe Thr Asn Asn Cys Tyr Arg Asp Ala Ile Val Thr Thr Ser Ile
            340                 345                 350
Asn Ser Leu Thr Ser Phe Ser Ser Gly Phe Val Val Phe Ser Phe Leu
            355                 360                 365
Gly Tyr Met Ala Gln Lys His Ser Val Pro Ile Gly Asp Val Ala Lys
        370                 375                 380
Asp Gly Pro Gly Leu Ile Phe Ile Ile Tyr Pro Glu Ala Ile Ala Thr
385                 390                 395                 400
Leu Pro Leu Ser Ser Ala Trp Ala Val Phe Phe Ile Met Leu Leu
            405                 410                 415
Thr Leu Gly Ile Asp Ser Ala Met Gly Gly Met Glu Ser Val Ile Thr
            420                 425                 430
Gly Leu Ile Asp Glu Phe Gln Leu Leu His Arg His Arg Glu Leu Phe
        435                 440                 445
Thr Leu Phe Ile Val Leu Ala Thr Phe Leu Leu Ser Leu Phe Cys Val
        450                 455                 460
Thr Asn Gly Gly Ile Tyr Val Phe Thr Leu Leu Asp His Phe Ala Ala
465                 470                 475                 480
Gly Thr Ser Ile Leu Phe Gly Val Leu Ile Glu Ala Ile Gly Val Ala
            485                 490                 495
Trp Phe Tyr Gly Val Gly Gln Phe Ser Asp Asp Ile Gln Gln Met Thr
        500                 505                 510
Gly Gln Arg Pro Ser Leu Tyr Trp Arg Leu Cys Trp Lys Leu Val Ser
        515                 520                 525
Pro Cys Phe Leu Leu Phe Val Val Val Ser Ile Val Thr Phe Arg
            530                 535                 540
Pro Pro His Tyr Gly Ala Tyr Ile Phe Pro Asp Trp Ala Asn Ala Leu
545                 550                 555                 560
Gly Trp Val Ile Ala Thr Ser Ser Met Ala Met Val Pro Ile Tyr Ala
            565                 570                 575
Ala Tyr Lys Phe Cys Ser Leu Pro Gly Ser Phe Arg Glu Lys Leu Ala
            580                 585                 590
Tyr Ala Ile Ala Pro Glu Lys Asp Arg Glu Leu Val Asp Arg Gly Glu
        595                 600                 605
Val Arg Gln Phe Thr Leu Arg His Trp Leu Lys Val
        610                 615                 620
```

COMPOSITIONS AND METHODS FOR MODULATING DOPAMINE NEUROTRANSMISSION

FIELD OF INVENTION

The present invention relates to compositions and methods for diagnosis or treatment of diseases or disorders involving abnormal dopamine neurotransmission. More particularly, the present invention relates to modulating dopamine transporter activity.

BACKGROUND OF THE INVENTION

The monoamine neurotransmitter dopamine (DA) plays a major role in regulating motor behavior, learning, reward and emotion (1, 2). Many neurological/neuropsychiatric disorders implicate a hyper-dopaminergic state in the etiology and/or maintenance of the disease (2-5). For example, U.S. Publication 2005/0048042 describes modulation of dopamine levels in the treatment of schizophrenia and addictive disorders. Recent SPECT and PET studies have confirmed an abnormally heightened level of synaptic dopamine in schizophrenia (6, 7).

Regulation of synaptic dopamine (DA) levels is predominantly regulated through active re-uptake by the dopamine transporter (DAT). Although previous studies have suggested the functional modulation of DAT by the dopamine D2 receptor (8-11) the molecular pathway underlying this process is yet unidentified. As the D2 receptor is a member of the G-protein coupled receptor (GPCR) family, any D2 receptor induced modulations are traditionally thought to be a sole product of protein phosphorylation via downstream activation of a second messenger cascade. However, in recent years, traditional concepts have been challenged with the identification of direct protein-protein interactions between two structurally and functionally distinct receptor families (12, 13).

Certain drugs increase dopamine concentrations by preventing dopamine reuptake, leaving more dopamine in the synapse. An example is the widely abused stimulant drug, cocaine. Another example is methylphenidate, used therapeutically to treat childhood hyperkinesis and symptoms of narcolepsy.

PCT Publication WO930826 discloses cloning of a cDNA encoding a dopamine transporter. Cells transfected with the cloned cDNA were observed to acquire dopamine uptake ability with the uptake by such transfected cells inhibitable by various uptake-inhibiting drugs. U.S. Pat. No. 6,218,595 discloses dopamine transporter knockout mice. Cells from these mice were observed to have decreased dopamine uptake. However, neither of these patent documents disclose a practical means for modulating dopamine activity.

A compound that could modulate dopamine activity could be used for treatment of core attention deficits seen in acute schizophrenics as well as treating addictive disorders such as addictions to cocaine or amphetamine.

At present, there are very few compounds available that are safe for mammalian administration and are selective for a dopamine transporter or receptor. For example, U.S. Patent Publication 20040077706 describes heterocyclic compounds that may be used to modulate activity of monoamine neurotransmitters, specifically dopamine, serotonin or norepinepherine. The use of the compounds for treating a variety of neurological or neuropsychiatric disorders relating to dopamine activity is suggested. However, none of the described compounds are shown to be selective for dopamine receptors or transporters.

Dopamine plays a major role in addiction. Regulation of dopamine plays a crucial role in mental and physical health. Neurons containing the neurotransmitter dopamine are clustered in the midbrain in an area called the *substantia nigra*. In Parkinson's disease, dopamine-transmitting neurons degenerate and the disease is marked by a progressive loss of dopamine production. Dopamine is involved in the reinforcing effects of natural rewards and is implicated in obesity. Thus, dopamine is involved in many physiological processes. However, there are very few small molecule compounds that selectively affect dopamine activity without impacting on other neurotransmitters, particularly monoamine neurotransmitters such as serotonin. There is a need for compounds that selectively modulate dopamine neurotransmission in the treatment of neurological or neuropsychiatric disorders, conditions or diseases in mammals.

Another problem in the present treatment of neurological disorders is resistance to drug therapy, for example in clinically diagnosed cases of depression. Thus, there is a need for new compounds and products that can modulate dopamine neurotransmission.

SUMMARY OF THE INVENTION

The present invention relates to compositions and methods for diagnosis or treatment of diseases or disorders involving abnormal dopamine neurotransmission. More particularly, the present invention relates to modulating dopamine transporter activity.

It is an object of the invention to provide an improved method for modulating dopamine uptake. Furthermore, the present invention provides methods for diagnosing or treating diseases involving abnormal levels of dopamine, and provides methods for modulating dopamine transporter activity.

According to the present invention there is provided a method for increasing dopaminergic neurotransmission in a mammal in need of such treatment comprising administering a therapeutically effective amount of an agent that disrupts D2-DAT coupling in a mammal. In certain non-limiting examples, the method is for treating a disease selected from the group consisting of cocaine addiction, amphetamine addiction, depression, obesity, ADHD, narcolepsy, and Parkinson's disease. The agent may be any small molecule chemical compound, polypeptide, nucleic acid, or any combination thereof, and further may optionally be linked or fused to a protein transduction domain. For example, the agent may be an antibody that binds to an amino acid sequence that comprises between about 80% and 100% identity to the sequence of D2 [IL3-2-5] (SEQ ID NO: 1) or the sequence of DAT[NT1-1] (SEQ ID NO:2). In another example, the agent may be a nucleic acid encoding a polypeptide of between about 7 amino acids and less than about 110 amino acids comprising an amino acid sequence that is between about 80% and 100% identical to the sequence of D2[IL3-2-5] (SEQ ID NO:1) or the sequence of DAT[NT1-1] (SEQ ID NO:2). In still another example, the agent may be a polypeptide of between about 7 amino acids and less than about 110 amino acids comprising an amino acid sequence that is between about 80% and 100% identical to the sequence of D2[IL3-2-5] (SEQ ID NO: 1) or the sequence of DAT [NT1-1] (SEQ ID NO:2). The sequence of D2[IL3-2-5] (SEQ ID NO: 1) extends from I311 to Q344 in reference to FIG. 6A.

The sequence of DAT[NT1-1] (SEQ ID NO:2) extends from M1 to V15 in reference to FIG. 5, and is underlined in this figure.

According to the present invention there is also provided a method for reducing dopaminergic neurotransmission in a mammal in need of such treatment comprising administering a therapeutically effective amount of an agent that localizes DAT at the cell surface. In one example, the method is for treating a disease selected from the group consisting of schizophrenia, and Tourette's syndrome. The agent may be any small molecule chemical compound, polypeptide, nucleic acid, or any combination thereof, and further may optionally be linked or fused to a protein transduction domain. For example, the agent may be a nucleic acid encoding a D2 receptor or a derivative thereof that is between about 70% and 100% identical to the D2 receptor and that maintains DAT-coupling activity. In another example, the agent may be a polypeptide comprising a D2 receptor or a derivative thereof that exhibits between at least 70% and 100% identity to the D2 receptor and that maintains DAT-coupling activity.

While full-length DAT or full-length D2 receptor may be used in the context of the present invention, fragments of DAT or fragments of D2 receptor may also be used. Polypeptides comprising a DAT fragment or a D2 receptor fragment can be of any length. For example, a polypeptide of 300, 250, 200, 150, 100, 90, 80, 70, 60, 50, 40, 30, 20, or less than any number therebetween, amino acids in length is contemplated. In one non-limiting example, the agent for use in the context of the present invention may be a polypeptide comprising an amino acid sequence that is identical to a sequence selected from the group consisting of D2[IL3-2] corresponding to amino acids E242-Q344 inclusive (SEQ ID NO:3), D2[IL3-2-3] corresponding to amino acids E297-Q344 inclusive (SEQ ID NO:4), D2[IL3-2-5] corresponding to amino acids I311-Q344 inclusive (SEQ ID NO: 5), DAT[NT] corresponding to amino acids M1-D68 inclusive (SEQ ID NO:6), DAT[NT1] corresponding to amino acids M1-P26 inclusive (SEQ ID NO:7), DAT[NT1-1] corresponding to amino acids M1-V15 inclusive (SEQ ID NO:2) or DAT [NT1-2] corresponding to amino acids A16-P26 (SEQ ID NO:11). Amino acid numbering of these exemplary fragments is in accordance with D2 short isoform sequence shown in FIG. 6A or DAT sequence shown in FIG. 5.

According to the present invention there is also provided a method of diagnosing schizophrenia or depression in a patient comprising determining whether cell surface localization of DAT in a test sample from the patient is less than in control samples. Cell surface localization of DAT may be determined by any convenient method known to persons skilled in the art. For example, cell surface localization of DAT is determined by quantifying dopamine uptake, by immunolabeling with an antibody specific for DAT, by coimmunoprecipitation of DAT with an antibody specific for D2 receptor, by affinity precipitation of DAT with a D2 receptor, by quantifying DAT ligand binding.

According to the present invention there is also provided a polypeptide of less than 110 amino acids comprising an amino acid sequence that is at least 80% identical to the sequence of D2[IL3-2-5] (SEQ ID NO: 1) or the sequence of DAT[NT1-1] (SEQ ID NO:2). For example, the polypeptide may comprise an amino acid sequence that is at least 80% identical to a sequence selected from the group consisting of D2[IL3-2] (SEQ ID NO:3), D2[IL3-2-3] (SEQ ID NO:4), D2[IL3-2-5] (SEQ ID NO: 1), DAT[NT] (SEQ ID NO:6), DAT[NT1] (SEQ ID NO:7), DAT[NT1-1] (SEQ ID NO:2) and DAT[NT1-2] (SEQ ID NO:11).

According to the present invention there is also provided a nucleic acid encoding a polypeptide of less than 110 amino acids comprising an amino acid sequence that is at least 80% identical to the sequence of D2[IL3-2-5] (SEQ ID NO: 1) or the sequence of DAT[NT1-1] (SEQ ID NO:2). For example, the nucleic acid may encode a polypeptide that comprises an amino acid sequence that is at least 80% identical to a sequence selected from the group consisting of D2[IL3-2] (SEQ ID NO:3), D2[IL3-2-3] (SEQ ID NO: 4), D2[IL3-2-5] (SEQ ID NO: 5), DAT[NT] (SEQ ID NO:6), DAT[NT1] (SEQ ID NO:7), DAT[NT1-1] (SEQ ID NO:2), and DAT[NT1-2] SEQ ID NO: 11.

A protein transduction domain may be fused or linked to any small molecule chemical compound, polypeptide, nucleic acid, or combination thereof, used in the context of the present invention. In certain non-limiting representative examples, the protein transduction domain is selected from the group consisting of TAT, and SynB1/3Cit.

As described herein, a direct interaction between D2 receptor and DAT, has been identified, and the present invention provides agents that specifically disrupt this to interaction. Furthermore, the present invention provides methods for identifying agents that disrupt the interaction between the D2 receptor and DAT.

Accordingly, the present invention provides a method for modulating dopaminergic neurotransmission. The direct D2-DAT interaction not only sheds light on a molecular pathway involved the regulation of DAT by the D2 receptor but also contributes to our understanding of how both these dopaminergic proteins may be involved in the etiology of neurological or neuropsychiatric disease, for example, but not limited to, schizophrenia. The ability of the D2 receptor to physically couple to the DAT and upregulate DAT activity by increasing DAT localization at the plasma membrane provides a novel method by which D2 receptors may facilitate the recruitment of DAT to synaptic regions. Disruption of this interaction can lead to impaired clearance of synaptic DA and provides a novel method for increasing levels of synaptic DA.

This summary of the invention does not necessarily describe all features of the invention.

BRIEF DESCRIPTION OF THE DRAWINGS

These and other features of the invention will become more apparent from the following description in which reference is made to the appended drawings wherein:

FIGS. 6A and B shows the amino acid sequence of short (A) and long (B) isoforms of human D2 receptor in accordance with a further embodiment of the present invention.

DETAILED DESCRIPTION

Figure 1:
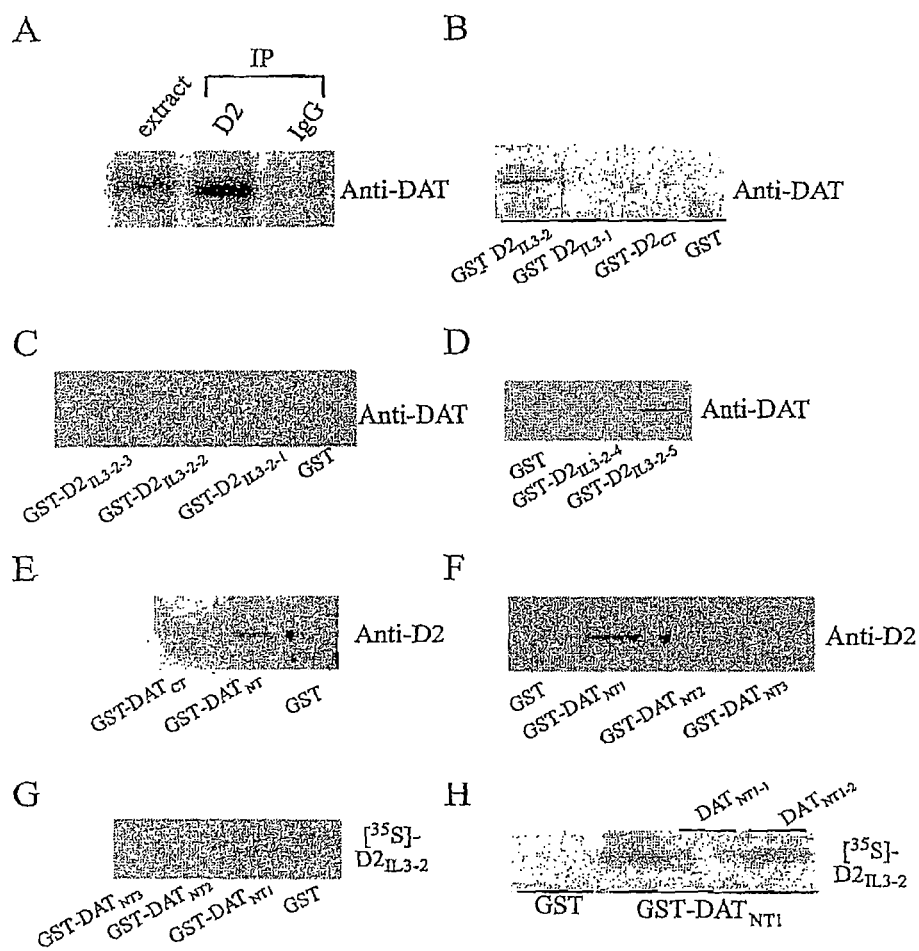
FIGS. 1A-H shows a direct interaction between D2 receptor and dopamine transporter (DAT) in accordance with an embodiment of the present invention. (A) Co-immunoprecipitation of DAT from solubilized rat striatal tissue with the D2 receptor. (B-D) Western blots for the DAT after affinity precipitation by GST fusion protein encoding D2[IL3-2] (SEQ ID NO: 3) (B); D2[IL3-2-3] (SEQ ID NO: 4) (C), and D2[IL3-2-5] (SEQ ID NO: 5) (D). Western blots of D2 receptors after affinity precipitation by GST fusion proteins encoding DAT[NT] (SEQ ID NO: 6) (E) and DAT[NT1] (SEQ ID NO: 7) (F). (G) In vitro binding assay showing the direct binding of GST-DAT[NT1] to [35S]-D2[IL3-2] wherein DAT [NT-1] is SEQ ID NO: 7 and D2[IL3-2] is SEQ ID NO:3. (H) In vitro binding assay displaying the blockade of direct binding of GST-DAT[NT1] to [35S]-D2[IL3-2] upon the addition of DAT[NT1-1] peptide.

The present invention relates to compositions and methods for diagnosis or treatment of diseases or disorders involving abnormal dopamine neurotransmission. The present invention also relates to compositions and methods for modulating dopamine transporter activity.

The following description is of a preferred embodiment.

Dopamine (DA) is known to be involved in various neurological or neuropsychiatric diseases, for example, without limitation, Parkinson's disease, attention deficit disorder, schizophrenia, and drug abuse. Dopamine transporter (DAT) is a cell surface transport protein that modulates synaptic DA concentrations by uptake of DA that has been released during the process of neurotransmission.

Rat, cow, and human DAT cDNAs have been cloned, with predicted amino acid sequences that DAT is a 619 (rat) or 620 (human) amino acid protein. DAT includes 12 transmembrane domains, with both the amino- and carboxy-termini being cytoplasmic.

DAT has been shown to have binding affinities for psychostimulants such as cocaine, amphetamine and methamphetamine, and further binding of these psychostimulants is correlated with prevention or reversal of DA uptake and behavioral activation (increased locomotor activity and/or stereotyped behaviors).

DAT knockout mice show higher levels of synaptic DA (5 fold) and for prolonged periods of time (100-300 fold). Further, these mice demonstrate locomotor hyperactivity akin to administration of psychostimulants in normal mice. The hyperactivity of knockout mice is not significantly increased with the administration of cocaine or amphetamine.

The present invention provides a method for modulating dopaminergic neurotransmission, partially as a result of identifying a direct interaction between D2 receptor and DAT (see Examples). Agents that specifically disrupt the interaction between the D2 receptor and DAT interaction, and methods for identifying agents that disrupt this interaction are provided. The ability of the D2 receptor to physically couple to the DAT and upregulate DAT activity by increasing DAT localization at the plasma membrane provides a novel method by which D2 receptors may facilitate the recruitment of DAT to synaptic regions. Disruption of this interaction can lead to impaired clearance of synaptic DA and provides a novel method for increasing levels of synaptic DA.

In an embodiment of the present invention, which is not meant to be limiting in any manner, the compounds and compositions of the present invention that increase dopaminergic neurotransmission could be used for any human disease that benefits from dopaminergic stimulation, for example, but not limited to Parkinson's disease, attention deficit hyperactivity disorder (ADHD), narcolepsy, depression, obesity, and psychostimulant addiction including, without limitation cocaine addiction and amphetamine addiction.

It is known in the art that Parkinson's disease is caused by decreased dopaminergic neurotransmission and drugs which increase or enhance dopaminergic neurotransmission are effective in treatment of the disorder (34). Narcolepsy is caused by a malfunction of the sleep-wake regulating system of the brain which can be characterized by symptoms including excessive daytime sleepiness, sleep attacks and cataplexy. Drugs which increase or enhance dopaminergic neurotransmission, for example, but not limited to amphetamines, are effective in the treatment of narcolepsy (35). Depression, obesity, and ADHD are diseases in which decreased dopaminergic neurotransmission is suspected. Indeed, drugs that increase dopaminergic neurotransmission are often effective in treating such diseases. For example, the drug buprorion which increases the activity of the dopamine system has shown good results in treating depression (31). In obesity, drugs that increase dopaminergic neurotransmission, for example, but not limited to amphetamines are effective as appetite suppressants (32). Similarly, such drugs are also effective in the treatment of ADHD (33). In cases of psychostimulant addiction, for example, but not limited to cocaine addiction and amphetamine addiction, postmortem brain studies have shown that brain dopamine levels are modestly decreased in human cocaine users and markedly decreased in human methamphetamine users. (38, 39). Thus drugs which increase or enhance dopaminergic neurotransmission may be useful in treating such addictions.

In an alternate embodiment of the present invention, which is not meant to be limiting, the compounds and compositions of the present invention that decrease go dopaminergic neurotransmission could be used for any human disease that benefits from decreased dopaminergic activity, for example, but not limited to schizophrenia and Tourette's syndrome.

It is known in the art that drugs that decrease dopaminergic neurotransmission, for example, but not limited to antipsychotics are effective in the treatment of schizophrenia (36). Similarly, such drugs are partially effective in the treatment of Tourette's syndrome (37).

Administration of an agent of the present invention, or agents identified using methods of the present invention to animal models results in disruption of the D2-DAT direct protein-protein interaction and results in hyperlocomotion in these model systems. In addition, a significant decrease in the D2-DAT interaction is observed in post-mortem brain tissue of schizophrenia patients compared to control subjects. Given that the protein expression level of D2 receptors in schizophrenia samples do not display any significant difference compared to control samples, decreased D2-DAT interaction in schizophrenics results from a disparity in the subcellular localization of the D2 receptors and DAT. Although there is a strong genetic component to many neurological, neuropsychiatric or both neurological and neuropsychiatric diseases, for example but not limited to, schizophrenia, it has become increasingly apparent that there are many contributing factors. The interaction between the D2-DAT contributes to our understanding of the diversity and complexity of the biomolecular mechanisms underlying these neurological, neuropsychiatric or both, disorders.

By "agent" it is meant any small molecule chemical compound, polypeptide, nucleic acid, or any combination thereof that can modulate dopaminergic neurotransmission. By "modulate dopaminergic neurotransmission" it is meant increasing dopaminergic neurotransmission or decreasing dopaminergic neurotransmission, for example, but not wishing to be limiting in any manner, by disrupting D2-DAT coupling or promoting localization of DAT at the cell surface. A polypeptide may be of any length unless otherwise specified and includes, for example and without limitation, antibodies, enzymes, receptors, transporters, D2 receptor, DAT, D2 receptor fragment or derivative, or DAT fragment or derivative. A fragment is any polypeptide or nucleic acid that is shorter than its corresponding naturally occurring polypeptide or nucleic acid, respectively. A derivative is any polypeptide or nucleic acid that is altered with respect to a reference polypeptide or nucleic acid, respectively, and includes, for example fragments or mutants.

Accordingly, the present invention provides a polypeptide of less than 110 amino acids comprising an amino acid sequence that is at least 80% identical to the sequence of D2[IL3-2-5] (SEQ ID NO: 1) or a fragment thereof, or the sequence of DAT[NT1-1] (SEQ ID NO:2) or a fragment thereof. In a preferred embodiment, the polypeptide is between about 7 and about 110 amino acids, for example, but not limited to 7, 8, 9, 10, 11, 12, 13, 14, 15, 17, 19, 20, 25, 30, 35, 40, 45, 50, 55, 60, 65, 70, 75, 80, 90 or 100 amino acids. In an alternate embodiment, the polypeptide is between about 15 and about 110 amino acids. However, it is to be understood that the size of the peptide may be defined by a range of any two of the values listed above. Also, in an alternate embodiment, which is not meant to be limiting in any manner, the present invention contemplates polypeptides as defined above which comprises more than 110 amino acids.

Figure 5:
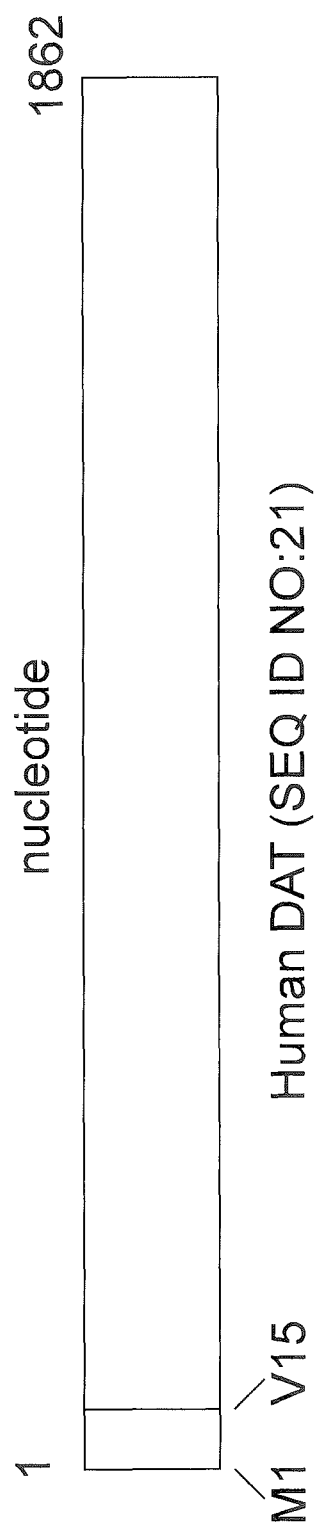
FIG. 5 shows the DAT coding sequence and amino acid sequence in accordance with a further embodiment of the present invention. The DAT[NT1-1] sequence (SEQ ID NO:2) is underlined.

The sequence of D2[IL3-2-5] (SEQ ID NO: 1) extends from I311 to Q344 inclusive in reference to FIG. 6A. The sequence of DAT[NT1-1] (SEQ ID NO: 2) extends from M1 to V15 in reference to FIG. 5, and is underlined in this figure. In a non-limiting example, the polypeptide of less than 110 amino acids may comprise an amino acid sequence that is at least 80% identical to the sequence of D2[IL3-2] (SEQ ID NO:3) extending from E242 to Q344 inclusive of FIG. 6, D2[IL3-2-3] (SEQ ID NO:4) extending from E297 to Q344 inclusive of FIG. 6, DAT[NT] (SEQ ID NO: 6) extending from M1 to D68 inclusive of FIG. 5, DAT[NT1] (SEQ ID NO:7) extending from M1-P26 inclusive of FIG. 5, and DAT [NT1-1] (SEQ ID NO: 2) extending from M1 to V15 inclusive of FIG. 5.

The present invention also contemplates polypeptides having an amino acid sequence that comprises 80%, 81%, 82%, 83%, 84%, 85%, 86%, 87%, 88%, 89%, 90%, 91%, 92%, 93%, 94%, 95%, 96%, 97%, 98%, 99% or 100% identity to the amino sequences described above. Further, the polypeptides may be defined as comprising a range of sequence identity defined by any two of the values listed above.

The present invention also provides a nucleic acid encoding polypeptides as defined above. For example, but not wishing to be limiting in any manner, the present invention contemplates a nucleic acid encoding a polypeptide of between about 7 and less than 110 amino acids, for example, but not limited to between 10 and 109 amino acids, between 10 and 100 amino acids, between 15 and 109 amino acids or between 15 and 100 amino acids and that encodes an amino acid sequence that is at least 80% identical to the sequence of D2[IL3-2-5] (SEQ ID NO: 1) or the sequence of DAT[NT1-1] (SEQ ID NO:2). In an alternate embodiment, the present invention contemplates nucleic acids or nucleotide sequences as described above but that encode more than 110 amino acids.

By "percent identical" or "percent indentity", it is meant one or more than one nucleic acid or amino acid sequence that is substantially identical to a coding sequence or amino acid sequence of peptides that can modulate dopaminergic neurotransmission. By "substantially identical" is meant any nucleotide sequence with similarity to the genetic sequence of a nucleic acid of the invention, or a fragment or a derivative thereof. The term "substantially identical" can also be used to describe similarity of polypeptide sequences. For example, nucleotide sequences or polypeptide sequences that are at least 70%, 75%, 80%, 85%, 90%, 92%, 95%, 96%, 98% or 99% identical to the D2 receptor or DAT coding sequence, or the encoded polypeptide, respectively, or fragments or derivatives thereof, and still retain ability to affect D2-DAT coupling or modulate dopaminergic neurotransmission are contemplated.

To determine whether a nucleic acid exhibits identity with the sequences presented herein, oligonucleotide alignment algorithms may be used, for example, but not limited to a BLAST (GenBank, using default parameters: Program: blastn; Database: nr; Expect 10; filter: default; Alignment: pairwise; Query genetic Codes: Standard(1)), BLAST2 (EMBL using default parameters: Matrix BLOSUM62; Filter: default, echofilter: on, Expect: 10, cutoff: default; Strand: both; Descriptions: 50, Alignments: 50), or FASTA, search, using default parameters. Polypeptide alignment algorithms are also available, for example, without limitation, BLAST 2 Sequences (using default parameters Program: blastp; Matrix: BLOSUM62; Open gap (11) and extension gap (1) penalties; gap x_dropoff: 50; Expect 10; Word size: 3; filter: default).

An alternative indication that two nucleic acid sequences are substantially identical is that the two sequences hybridize to each other under moderately stringent, or preferably stringent, conditions. Hybridization to filter-bound sequences under moderately stringent conditions may, for example, be performed in 0.5 M $NaHPO_4$, 7% sodium dodecyl sulfate (SDS), 1 mM EDTA at 65° C., and washing in 0.2×SSC/0.1% SDS at 42° C. for at least 1 hour (see Ausubel, et al. (eds), 1989, Current Protocols in Molecular Biology, Vol. 1, Green Publishing Associates, Inc., and John Wiley & Sons, Inc., New York, at p. 2.10.3). Alternatively, hybridization to filter-bound sequences under stringent conditions may, for example, be performed in 0.5 M $NaHPO_4$, 7% SDS, 1 mM EDTA at 65° C., and washing in 0.1×SSC/0.1% SDS at 68° C. for at least 1 hour (see Ausubel, et al. (eds), 1989, supra). Hybridization conditions may be modified in accordance with known methods depending on the sequence of interest (see Tijssen, 1993, Laboratory Techniques in Biochemistry and Molecular Biology—Hybridization with Nucleic Acid Probes, Part I, Chapter 2 "Overview of principles of hybridization and the strategy of nucleic acid probe assays", Elsevier, N.Y.). Generally, but not wishing to be limiting, stringent conditions are selected to be about 5° C. lower than the thermal melting point for the specific sequence at a defined ionic strength and pH.

By protein transduction domain it is meant a sequence of nucleic acids that encode a polypeptide, or a sequence of amino acids comprising the polypeptide, wherein the polypeptide facilitates localization to a particular site, for example a cell or the like, or it may facilitate transport across a membrane or lipid bilayer. The polypeptides and nucleic acids of the present invention may be fused to a protein transduction domain to facilitate transit across lipid bilayers or membranes.

Many polypeptides and nucleic acids do not efficiently cross the lipid bilayer of the plasma membrane, and therefore enter into cells at a low rate. However, there are certain naturally occurring polypeptides that can transit across membranes independent of any specific transporter. Antennapedia (Drosophila), TAT (HIV) and VP22 (Herpes) are examples of such polypeptides. Fragments of these and other polypeptides have been shown to retain the capacity to transit across lipid membranes in a receptor-independent fashion. These fragments, termed protein transduction domains, are generally 10 to 27 amino acids in length, possess multiple positive charges, and in several cases have been predicted to be ampipathic. Polypeptides and nucleic acids that are normally inefficient or incapable of crossing a lipid bilayer, can be made to transit the bilayer by being fused to a protein transduction domain.

U.S. Publication 2002/0142299 (which is incorporated herein by reference) describes a fusion of TAT with human beta-glucuronidase. This fusion protein readily transits into various cell types both in vitro and in vivo. Furthermore, TAT fusion proteins have been observed to cross the blood-brain-barrier. Frankel et al. (U.S. Pat. No. 5,804,604, U.S. Pat. No. 5,747,641, U.S. Pat. No. 5,674,980, U.S. Pat. No. 5,670,617, and U.S. Pat. No. 5,652,122; which are incorporated herein by reference) have also demonstrated transport of a protein (beta-galactosidase or horseradish peroxidase) into a cell by fusing the protein with amino acids 49-57 of TAT.

PCT publication WO01/15511 (which is incorporated herein by reference) discloses a method for developing protein transduction domains using a phage display library. The method comprises incubating a target cell with a peptide display library and isolating internalized peptides from the cytoplasm and nuclei of the cells and identifying the peptides. The method further comprised linking the identified peptides to a protein and incubating the peptide-protein complex with a target cell to determine whether uptake is facilitated. Using this method a protein transduction domain for any cell or tissue type may be developed. US Publication 2004/0209797 (which is incorporated herein by reference) shows that reverse isomers of several of the peptides identified by the above can also function as protein transduction domains.

PCT Publication WO99/07728 (which is incorporated herein by reference) describes linearization of protegrin and tachyplesin, naturally occurring as a hairpin type structure held by disulphide bridges. Irreversible reduction of disulphide bridges generated peptides that could readily transit cell membranes, alone or fused to other biological molecules. US Publication 2003/0186890 (which is incorporated herein by reference) describes derivatives of protegrin and tachyplesin that were termed SynB1, SynB2, SynB3, etc. These SynB peptides were further optimized for mean hydrophobicity per residue, helical hydrophobic moment (amphipathicity), or beta hydrophobic moment. Various optimized amphipathic SynB analog peptides were shown to facilitate transfer of doxorubicin across cell membranes. Further, doxorubicin linked to a SynB analog was observed to penetrate the blood-brain-barrier at 20 times the rate of doxorubicin alone.

The protein transduction domains described in the proceeding paragraphs are only a few examples of the protein transduction domains available for facilitating membrane transit of small molecules, polypeptides or nucleic acids. Other examples are transportan, W/R, AlkCWK18, DipaLytic, MGP, or RWR. Still many other examples will be recognized by persons skilled in the art.

A protein transduction domain and an agent of the present invention may be placed together in sufficient proximity and maintained together for a sufficient time to allow the protein transduction domain to influence pharmaceutical product performance of the agent. Contemplated associations of protein transduction domain and agent include, for example and without limitation: non-covalent associations such as electrostatic interactions, hydrogen bonding, ionic bonds or complexes, Van der Waals bonds; covalent linkages such as conventional methods of cross-linking; linkages that are activated, in vitro and/or in vivo by electromagnetic radiation; any covalent bond such as a peptide bond; any biochemical interaction known to protein biochemists, such as biotin/streptavidin, nickel/Histidine, glutathione/glutathione-S-transferase, or antigen/antibody; physical associations within matrix structures or encapsulating systems; etc.

The present invention provides an agent that may be any small molecule chemical compound, polypeptide, nucleic acid, or any combination thereof that can modulate dopaminergic neurotransmission by either disrupting D2-DAT coupling or promoting localization of DAT at the cell surface. Accordingly, the present invention provides a polypeptide of about 7 to less than about 110 amino acids, preferably 10 to 109 amino acids, more preferably 15 to 100 amino acids and comprising an amino acid sequence that is at least 80% identical, for example, but not limited to 80%, 85%, 90%, 95%, 96%, 97%, 98%, 99%, or 100% identical to the sequence of D2[IL3-2-5] (SEQ ID NO:1) or the sequence of DAT[NT1-1] (SEQ ID NO: 2). The present invention also provides a nucleic acid encoding a polypeptide of about 7 to less than about 110 amino acids, preferably about 10 to about 109 amino acids, more preferably about 15 to about 100 amino acids and comprising an amino acid sequence that is at least 80% identical, for example, but not limited to 80%, 85%, 90%, 95%, 96%, 97%, 98%, 99%, or 100% identical to the sequence of D2[IL3-2-5] (SEQ ID NO:1) or the sequence of DAT[NT1-1] (SEQ ID NO:2). The polypeptide or nucleic acid may optionally be fused to a protein transduction domain.

A polypeptide of the invention can be synthesized in vitro or delivered to a cell in vivo by any conventional method. As a representative example of an in vitro method, the polypeptide may be chemically synthesized in vitro, or may be enzymatically synthesized in vitro in a suitable biological expression system, such as without limitation, wheat germ extract or rabbit reticulocyte lysate. As a representative example of an in vivo method, a DNA, RNA, or DNA/RNA hybrid molecule comprising a nucleotide sequence encoding a polypeptide of the invention is introduced into an animal, and the nucleotide sequence is expressed within a cell of an animal.

The nucleotide sequence may be operably linked to regulatory elements in order to achieve preferential expression at desired times or in desired cell or tissue types. Furthermore, as will be known to one of skill in the art, other nucleotide sequences including, without limitation, 5' untranslated region, 3' untranslated regions, cap structure, poly A tail, translational initiators, sequences encoding signalling or targeting peptides, translational enhancers, transcriptional enhancers, translational terminators, transcriptional terminators, transcriptional promoters, may be operably linked with the nucleotide sequence encoding a polypeptide (see as a representative examples "Genes VII", Lewin, B. Oxford University Press (2000) or "Molecular Cloning: A Laboratory Manual", Sambrook et al., Cold Spring Harbor Laboratory, 3rd edition (2001)). A nucleotide sequence encoding a polypeptide or a fusion polypeptide comprising a polypeptide agent and a protein transduction domain may be incorporated into a suitable vector. Vectors may be commercially obtained from companies such as Stratagene or InVitrogen. Vectors can also be individually constructed or modified using standard molecular biology techniques, as outlined, for example, in Sambrook et al. (Cold Spring Harbor Laboratory, 3rd edition (2001)). A vector may contain any number of nucleotide sequences encoding desired elements that may be operably linked to a nucleotide sequence encoding a polypeptide or fusion polypeptide comprising a protein transduction domain. Such nucleotide sequences encoding desired elements, include, but are not limited to, transcriptional promoters, transcriptional enhancers, transcriptional terminators, translational initiators, translational, terminators, ribosome binding sites, 5' untranslated region, 3' untranslated regions, cap structure, poly A tail, origin of replication, detectable markers, affinity tags, signal or target peptide. Persons skilled in the art will recognize that the selection and/or construction of a suitable factor may depend upon several factors, including, without limitation, the size of the nucleic acid to be incorporated into the vector, the type of transcriptional and translational control elements desired, the level of expression desired, copy number desired, whether chromosomal integration is desired, the type of selection process that is desired, or the host cell or the host range that is intended to be transformed.

The DNA, RNA, or DNA/RNA hybrid molecule may be introduced intracellularly, extracellularly into a cavity, interstitial space, into the circulation of an organism, orally, or by any other standard route of introduction for therapeutic molecules and/or pharmaceutical compositions. Standard physical methods of introducing nucleic acids include, but are not limited to, injection of a solution comprising RNA, DNA, or RNA/DNA hybrids, bombardment by particles covered by the nucleic acid, bathing a cell or organism in a solution of the nucleic acid, or electroporation of cell membranes in the presence of the nucleic acid.

A nucleic acid may be introduced into suitable eukaryotic cells ex vivo and the cells harbouring the nucleic acid can then be inserted into a desired location in an animal. A nucleic acid can also be used to transform prokaryotic cells, and the transformed prokaryotic cells can be introduced into an animal, for example, through an oral route. Those skilled in the art will recognize that a nucleic acid may be constructed in such a fashion that the transformed prokaryotic cells can express and secrete a polypeptide of the invention. Preferably, the prokaryotic cell is part of the animal's endogenous intestinal microflora. With regards to human examples of endogenous microflora are, without wishing to be limiting, *Lactobacillus acidophillus, Streptococcus thermophilus*, and *Bifidobacterium bifidum*. A nucleic acid may also be inserted into a viral vector and packaged into viral particles for efficient delivery and expression.

Dosage Forms

An agent of the present invention, for example, DAT or D2 polypeptides or nucleic acids encoding these polypeptides or antibodies or small molecules capable of disrupting D2-DAT coupling, may be formulated into any convenient dosage form. The dosage form may comprise, but is not limited to an oral dosage form wherein the agent is dissolved, suspended or the like in a suitable excipient such as but not limited to water. In addition, the agent may be formulated into a dosage form that could be applied topically or could be administered by inhaler, or by injection either subcutaneously, into organs, or into circulation. An injectable dosage form may include other carriers that may function to enhance the activity of the agent. Any suitable carrier known in the art may be used. Also, the agent may be formulated for use in the production of a medicament. Many methods for the productions of dosage forms, medicaments, or pharmaceutical compositions are well known in the art and can be readily applied to the present invention by persons skilled in the art.

Combination therapy with agents of the present invention or other agents that affect monoamine neurotransmission is contemplated. With regards to combination therapy suitable dosage forms again include capsules, tablets, and the like, preferably for oral administration, although any dosage form, for any route of administration is contemplated. Combination therapy can be administered as separate entities, e.g. two tablets or other forms, each containing one agent, or may be administered as a single dosage form containing both drugs, or concomitant use.

In case of oral administration of two or more different agents, the single dose can be, but is not limited to a capsule, tablet, or oral solution, and it may also contain inactive component(s) that is necessary to form the single delivery system.

Combination therapy medications of the present invention may be administered by any desired route, for example without limitation, administration can be transdermal (patch), buccal, sublingual, topical, nasal, parenteral (subcutaneous, intramuscular, intravenous, intradermal), rectal, vaginal, administration. Various combinations of controlled release/rapid release are also contemplated.

Diagnosis and Treatment

The methods and compounds of the present invention are also useful for diagnosing diseases that are characterized by abnormal levels of cell surface localized DAT, for example, without limitation, Tourette's syndrome, schizophrenia, and depression.

The present invention provides a method of diagnosing schizophrenia or depression in a patient comprising determining whether cell surface localization of DAT in a test sample from the patient is less than that of a predetermined value, or when compared to the cell surface localization of DAT in a control sample.

Determining Localization of DAT

Direct quantification and localization of DAT protein in PD brains may be determined using DAT-specific antisera. Furthermore, a number of cocaine-related DAT ligands of high affinity and reasonable specificity have been developed for positron emission tomography (PET) and single photon emission computerized tomography (SPECT). 99 mTc-TRODAT-1, is a radiolabeled tropane and is a further example of a ligand that selectively binds to DAT.

Cell surface localization of DAT may be determined by any number of methods known in the art for example, quantifying dopamine uptake, immunolabeling with an antibody specific for DAT, coimmunoprecipitation of DAT with an antibody specific for D2 receptor, affinity precipitation of DAT with an immobilized D2 receptor, quantifying DAT ligand binding.

Furthermore, the methods and compounds of the present invention can be used to modulate dopaminergic neurotransmission and are therefore useful in treating any disease that is characterized by abnormal dopaminergic neurotransmission. The following are some non-limiting examples of such diseases.

Neurological, Neuropsychiatric Diseases

Tourette's syndrome is characterized by obsessions, compulsions, coprolalia and involuntary tics. DAT ligand binding in postmortem caudate-putamen from Tourette's syndrome subjects showed 37-50% increase in the density of DAT-ligand binding compared to controls. Furthermore, decreasing DA neurotransmission has been shown to ameliorate symptoms. The present invention teaches a direct interaction between D2 and DAT, and further discloses that expression of D2 receptors can increase cell surface localization of DAT. Accordingly, administration of agents of the present invention, for example, a D2 receptor or a derivative of a D2 receptor that maintains DAT-coupling activity can be useful in reducing DA neurotransmission and treating Tourette's syndrome.

Delusions, hallucinations, extreme emotions, excited motor activity, incoherent thoughts and speech, are some symptoms of Schizophrenia. Alterations in the Vmax and Km for DA uptake into cryopreserved nerve terminals from the striatum of schizophrenics relative to age- and sex-matched controls has been reported. Furthermore, recent SPECT and PET studies have confirmed an abnormally heightened level of synaptic DA in schizophrenia. Methods of the present invention have been shown to be useful in increasing DA uptake and may be used to treat a hyper-dopaminergic state in schizophrenics.

Depression is characterized by profound sadness, pronounced changes in sleep, appetite, and energy. Recurrent thoughts of death or suicide, persistent physical symptoms that do not respond to treatment, such as headaches, digestive disorders, and chronic pain are some symptoms of major depression. Major depression is a unipolar depression, while bipolar disorder (manic depression) involves both depression and mania. Early identification and treatment of depression is required to minimize risk of suicide and self-inflicted injury. Decreased DAT availability has been found to be associated with symptoms of depression or anxiety in Parkinson's disease patients. Decreased DAT levels can provide a marker for diagnosis of depression. Bupropion (Wellbutrin) classified as a dopamine reuptake inhibitor has shown good results in treating depression. The method and compounds of the present invention are useful in decreasing DA uptake by disrupting D2-DAT coupling and may be used for treating depression.

Variants of the dopamine D2 receptor gene have been associated with alcoholism, cocaine addiction, nicotine addiction, polysubstance abuse, and other drug dependencies. Psychostimulants such as cocaine, amphetamine, methamphetamine (speed), interfere with the normal regulation of DA by blocking or reversing DAT-mediated uptake, and thereby disabling the major clearance mechanism for DA. Nicotine increases synaptic DA by activating dopaminergic neurons. Cigarette smokers have also been shown to reduce levels of Monoamine oxidase B, which is involved in DA breakdown. Other addictive drugs such as alcohol and heroin also exert stimulatory effects via an increase in dopaminergic neurotransmission. The methods and products of the present invention that increase dopaminergic neurotransmission may be useful for treating patients addicted to a drug of abuse, so as to maintain heightened levels of extracellular DA during the withdrawal period.

Addiction to natural rewards includes pleasurable feelings from food as well as other natural rewards are thought to occur through an increase of extracellular DA levels. Drug induced elevation of DA has been shown to decrease food intake. PET studies have shown that obese subjects have fewer dopamine receptors than normal-weight subjects. Furthermore, within the obese subjects an inverse correlation between the number of dopamine receptors and the subjects' body mass index was established. Obesity is a burgeoning medical crisis and there is a need for compounds that can be administered to obese individuals to increase dopaminergic neurotransmission so as to decrease food consumption. Accordingly, the methods and products of the present invention that increase dopaminergic neurotransmission can be useful for treating obesity.

Attention-deficit hyperactivity disorder (ADHA) is characterized by a persistent pattern of abnormally high levels of activity, impulsivity, and/or inattention. ADHD appears to be familial and heritable, and is perhaps the most common childhood-onset behavioral disorder. It is well recognized that ADHD patients benefit from treatment with certain psychostimulants, such as methylphenidate (Ritalin) and amphetamine, which directly interact with the DAT. PET studies have shown that administering normal therapeutic doses of methylphenidate to healthy, adult men increased DA levels. The present invention provides methods for increasing dopaminergic neurotransmission that may be used for treating ADHD. For example, a polypeptide comprising an amino acid sequence that is identical or substantially identical to a sequence selected from the group consisting of D2[IL3-2] (SEQ ID NO:3), D2[IL3-2-3] (SEQ ID NO:4), D2[IL3-2-5] (SEQ ID NO:1), DAT[NT] (SEQ ID NO:6), DAT[NT1] (SEQ ID NO:7), and DAT[NT1-1] (SEQ ID NO:2) are useful for reducing DAT-mediated DA uptake and may be administered to a patient suffering from ADHD.

Parkinson's disease is characterized by a progressive loss of DA neurotransmission. The vulnerability of certain subgroups of DA neurons in Parkinson's correlates with higher basal levels of DAT gene expression. DAT may transport neurotoxins, and further transport of endogenous DA by DAT may exacerbate the loss of DA neurotransmission. Accordingly, the methods of increasing dopaminergic neurotransmission of the present invention may be useful in treating Parkinson's disease. Administration of the agents of the present invention, for example without limitation, a polypeptide of less than 110 amino acids comprising an amino acid sequence that is at least 80% identical to the sequence of D2[IL3-2-5] (SEQ ID NO:1) or the sequence of DAT[NT1-1] (SEQ ID NO:2), can at least partially compensate for loss in DA neurotransmission and may retard DA neuron loss.

Accordingly the present invention provides methods for modulating dopaminergic neurotransmission in a mammal. Any mammal including, without limitation, human, rat, cow, pig, dog, or mouse, may be treated with the agents and methods of the present invention.

The present invention will be further illustrated in the following examples.

EXAMPLES

Methods for Characterizing D2-DAT Interaction

GST Fusion Proteins and Mini-Genes: Dopamine D2-[CT], D2[IL3], D2[IL3-1], D2[IL3-2], D2[IL3-2-1] (SEQ ID NO:15), D2[IL3-2-2], D2[IL3-2-3], D2[IL3-2-4], D2[IL3-2-5] and DAT[CT], DAT[NT], DAT[NT1], DAT[NT2], DAT[NT3], DAT[NT1-1], DAT[NT1-2] cDNA-encoding fragments were amplified by PCR from full-length cDNA clones. All 5' and 3' oligo-nucleotides incorporated BamHI and EcoRI sites respectively to facilitate sub-cloning into pcDNA3 or pGEX4T-3. Initiation methionine residues and stop codons were also incorporated where appropriate. GST-fusion proteins were prepared from bacterial lysates as described by the manufacturer (Amersham). To confirm appropriate splice fusion and the absence of spurious PCR generated nucleotide errors, all constructs were re-sequenced.

Co-Immunoprecipitation, Protein Affinity Purification (Pull-Down) and Western Blotting Co-immunoprecipitation, affinity pull-down and Western blot analyses were performed as previously described (Liu et al., 2000; Lee et al., 2002a). Rat brain striatum (100 mg) were homogenized in buffer containing 50 mM Tris-Cl (pH 7.6), 150 mM NaCl, 1% igepalCA630, 0.5~1% sodium deoxycholate, 1% Triton X-100, 2 mM EDTA, 1 mM PMSF and protease inhibitor cocktail (Sigma 5 µl/100 mg tissue), centrifuged at 10,000×g at 4 degree C. for 20 mM, the supernatant was extracted and protein concentrations were measured (Pierce).

For coimmunoprecipitation experiments, solubilized hippocampal/cell extracts (50~700 µg) protein were incubated in the presence of primary antibodies anti-D1, anti-D2 (Chemicon) or IgG (1-2 µg) for 4 h at 4 degree C., followed by the addition of 20 µl of protein A/G agrose (Santa Cruz) for 12 h. Pellets were washed four times in buffer described above, boiled for 5 min in SDS sample buffer and subjected to SDS-PAGE. 20~50 µg of tissue extracted protein was used as control in each experiment.

For affinity purification experiments, solubilized hippocampal extracts (50-100 µg protein) were incubated with glutathione-Sepharose beads (Pharmacia) bound to the indicated GST-fusion proteins (50~100 µg) at room temperature for 1 hour. Beads were washed three times with 600 µl PBS containing 0.1-0.5% Triton X-100 before the bound proteins were eluted with glutathione elution buffer. Elutes were incubated in sample buffer and subjected to 10% SDS-PAGE for Western blot analysis.

Western blots. Blots were blocked with 5% non-fat dried milk dissolved in TBST buffer (10 mM Tris, 150 mM NaCl and 0.1% Tween-20) for 1 hour at room temperature, washed three times with TBST buffer, and then incubated with the appropriate primary antibody (anti-DAT, anti-D2: Chemicon, diluted in 0.1% milk in TBST) overnight at 4 deg C., washed again with TBST buffer three times and the membrane incubated with horseradish peroxidase conjugated secondary antibody (Sigma, diluted in 0.1% milk in TBST) for 1.5 hour at room temperature. The proteins were visualized with enhanced chemiluminescence reagents as described (Amersham).

In Vitro Binding Assays:

Glutathione beads carrying GST fusion proteins (DAT[NT1] (SEQ ID NO:7), DAT[NT2] (SEQ ID NO:9), DAT[NT3] (SEQ ID NO: 10)) or GST (10~20 µg each) alone was incubated with [35S]-methionine-labelled D2[IL3-2] probe (SEQ ID NO:3) respectively. The beads were then washed 4-6 times with PBS containing 0.5% Triton X-100 and eluted with 10 mM glutathione elution buffer. Eluates were separated by SDS-PAGE and visualized by autoradiography.

Cell-ELISA Assays:

Cell-ELISA assays (colorimetric assays) were done essentially as previously described (Lee et al., 2002a). Neurons or HEK-293T cells were transiently transfected with the indicated cDNA constructs by the Lipofectamine 2000 (InVitrogen) method (6-10 µg of each indicated cDNA per 7.5×10$^6$ cells), and equally distributed to two 6-well plates (35 mm/well), and grown for 2-4 days. The same density of co-transfected cells were fixed in 4% paraformaldehyde for 10 min in the absence (non-permeabilized conditions) or the presence (permeabilized conditions) of 1% Triton X-100. Cells were incubated with DAT antibody against the extracellular loop (Chemicon) for the purpose of labeling the proteins on the cell surface under non-permeabilized conditions or the entire transporter pool under permeabilized conditions. After incubation with corresponding HRP-conjugated secondary antibodies (Sigma), HRP substrate OPD (Sigma) was added to produce a color reaction that was stopped with 3N HCl. The cell surface expression of DAT was presented as the ratio of colorimetric readings under non-permeabilized conditions to those under permeabilized conditions. Analysis was done using at least 12 separate dishes in each group. Cell-ELISA assays using primary midbrain neurons were carried out identically with assays using HEK-293T cells.

[3H] DA Uptake Analysis:

Measurement of DA uptake was performed on intact cells as previously described (30). Briefly, 2-4 days following transfection in 24-well plates (~2×10$^5$ cells seeded per well) medium was removed and wells were rinsed with 0.5 mL of uptake buffer (5 mM Tris, 7.5 mM HEPES, 120 mM NaCl, 5.4 mM KCl, 1.2 mM CaCl$_2$, 1.2 mM MgSO$_4$, 1 mM ascorbic acid, 5 mM glucose, pH 7.1). Cells were then preincubated in duplicate with the indicated concentrations of dopaminergic agents ($10^{-13}$ to $10^4$ M) 5 min prior to the addition of 0.25 mL of 20 nM [3H]DA (final concentration) and incubated for 10 min at room temperature in a total volume of 0.5 mL. Non-specific [3H] DA (37-53 Ci/mmol) uptake was defined in the presence of 10 µM mazindol. Wells were rinsed twice with 0.5 mL of uptake buffer and cells were solubilized in 0.5 mL of 1% SDS and collected to measure incorporated radioactivity using a Beckman liquid scintillation counter (LS 6000SC).

[3H]CFT Binding:

Measurement of [3H] (2 beta-carbomethoxy-3 beta-(4-fluorophenyl)-tropane) ([3H]CFT) binding was performed on intact cells as previously reported (30) using conditions similar to those described above. Briefly, medium was removed and cells were rinsed with 0.5 mL of buffer, then incubated with 0.25 mL of buffer or drug for 5 min before the addition of 0.25 mL [3H]CFT (4 nM final concentration). After a 2 to 3 hour incubation at 4 deg C., cells were washed twice with 0.5 mL of ice-cold buffer, solubilized with 1% SDS and bound radioligand measured for radioactivity as described above. Most competition assays were performed using 12 different concentrations (in duplicate) of the drug. Nonspecific binding was determined in the presence of 10 µM mazindol or GBR12909.

For all experiments, direct assay comparisons between co-transfections and single transfections were conducted in parallel, using the same dilutions of drug, on the same batch of transfected cells.

Primary Midbrain Cultures:

Midbrain cultures from postnatal day 2 rats are prepared by dissection of ventrolateral sections of the mesencephalon (avoiding medial tissue regions) in ice-cold HBSS. Tissue is placed in cold neurobasal/B27 medium (Invitrogen) supplemented with 0.5 mM L-glutamine, and 10 ng/mL bFGF (culture medium). Tissue sections are mechanically dissociated either through trituration through a fire-polished Pasteur pipette or by gently passing the tissues through a sterile 70 micron nylon cell strainer using a sterile 3 cc syringe plunger. The single cell suspensions are counted with a hemocytometer for plating at desired densities onto poly-D-Lysine (100 ug/mL) coated tissue culture plates of varying formats or, onto coated glass cover-slips for microscopy. Cultures are incubated at 37 deg C. in a 5% CO$_2$ incubator in neurobasal-A/B27 medium for 10-14 days before infecting with recombinant adenovirus of D2 and DAT.

Recombinant Adenovirus Construction and Infection:

Recombinant adenoviruses were formed by co-transfecting cDNAs encoding the DAT in the shuttle vector pDC315 (Microbix) with replication-deficient adenovirus type 5 DNA into HEK-293T cells. The recombinant adenoviruses containing the DAT cDNAs were isolated, confirmed by PCR, plaque-purified, expanded and titered. For infection, primary midbrain cultures were infected with 10~20 plaque-forming units per neuron [multiplicity of infection (moi)] of recombinant adenovirus in 500 µl culture medium. Cultures were supplemented with 1.5 ml of fresh medium 1 hour after infection.

TAT Peptides Construction:

The midbrain cultures were treated with TAT-DAT peptides (1 hour, 10 µM) before [3H]DA uptake measurement. TAT-peptides were constructed by Chemicon, which include a dansyl tag at the amino-terminus to facilitate visualization of the intra-neuronal accumulation of the peptides. Peptides are rendered cell-permeant by fusing the D2[IL3-2C] PCR fragment to the cell-membrane transduction domain of the human immunodeficiency virus-type 1 TAT protein (YGRKKRRQRRR) (SEQ ID NO:14) as previously described (21). The TAT-peptide was applied to primary cultures directly (10 µM) for 1 hour. The primary culture was examined by fluorescent microscopy.

Laser Confocal Microscopy:

HEK-293T cells were transiently transfected with DAT, D2Short cDNA vectors (as indicated). At 48 hours post-transfection cells were fixed with 4% paraformaldehyde, blocked with 10% normal goat serum in 1×PBS and permeabilized with 0.2% Triton X-100. Afterwards cells were incubated with polyclonal DAT antibody (Santa Cruz) and monoclonal D2 antibody (Santa Cruz) for 16-18 hours upon which cells were incubated with anti-rabbit-FITC or anti-mouse-CY3 antibodies (Jackson Immunologicals) for 1-2 hours. Mounted coverslips were then examined with a laser confocal mcrocope Zeiss LSM510.

Locomotor Activity:

Tests of locomotor activity were conducted in four clear Plexiglas activity chambers (Med Associates Inc., St Albans, Vt.) measuring 43 cm long, 43 cm wide, and 30 cm high. An array of 16×16 photodetectors, spaced 2.5 cm apart, and positioned 2.5 cm above the floor of the chamber was used to detect horizontal locomotor activity as distance traveled. Prior to testing, all mice were first habituated to the apparatus by placing them in the activity chambers for 1 h on three consecutive days. On test days, mice were placed in the activity chamber for 1 h prior to receiving an IP injection of TAT (SEQ ID NO:14), TAT-DAT[NT1-1] (SEQ ID NO:12), or TAT-DAT[NT1-2] peptide (SEQ ID NO: 13). Locomotor activity was then measured for the next 180 min.

Example 1

D2 Receptor Fragments that Bind to DAT from Rat Striatal Tissue

To determine the existence of D2: DAT complexes, coimmunoprecipitatition of D2 receptor and DAT from rat striatal tissue was determined. As depicted in FIG. 1A, D2 receptor coimmunoprecipitated with DAT suggesting an interaction between the D2 receptor and DAT. The intracellular domains of both the D2 receptor and DAT contain putative consensus sequences for receptor phosphorylation and potential binding sites for various proteins important for signaling [e.g. α-synuclein, GRIP] (14-17). To determine which regions of the D2 and DAT are involved in the formation of D2: DAT complex, various glutathione-S-transferase (GST) fusion proteins, encoding the third intracellular loop (IL3) and the carboxyl tail (CT) of the D2 receptors (GST fused to D2[IL3-1]: K211-K241 (SEQ ID NO:5); GST fused to D2[IL3-2]: E242-Q344 (SEQ ID NO:3); GST fused to D2[CT]: T399-C414 (SEQ ID NO:8); amino acid numbering in accordance with D2 short isoform shown in FIG. 6A) were prepared and utilized in affinity purification assays. As shown in FIG. 1B, GST fused to D2[IL3-2] (SEQ ID NO:3), but not GST fused to D2[IL3-1] (SEQ ID NO:5), GST fused to D2-[CT] (SEQ ID NO:8) or GST alone, precipitated DAT from solubilized rat striatum indicating that DAT can interact with D2 receptor through portion of its third intracellular loop.

In order to confirm these results and to further delineate the region of the D2[IL3-2] (SEQ ID NO:3) involved in the D2-DAT interaction, three GST fusion proteins (D2[IL3-2-1]: E242-P271 (SEQ ID NO:15); D2[IL3-2-2]:S259-I311 (SEQ ID NO: 16); D2[IL3-2-3]:E297-Q344 (SEQ ID NO:4) encoding D2[IL3-2] (SEQ ID NO:3) were constructed. Affinity purification assays showed that GST fused to D2[IL3-2-3] (SEQ ID NO:4), but not GST fused to D2[IL3-2-1] (SEQ ID NO:15) or GST fused to D2[IL3-2-2] (SEQ ID NO:16), was able to precipitate solubilized DAT (FIG. 1C), suggesting that E297-Q344 region (SEQ ID NO:4) of the D2 receptor is required for the interaction with the DAT.

Since D2[IL3-2-2] (S259-I311) (SEQ ID NO:16) and D2[IL3-2-3] (E297-Q344) (SEQ ID NO:4) regions share overlapping sequence (E297-I311) and GST fused to D2[IL3-2-2] (SEQ ID NO: 16) failed to interact with DAT, the I311-Q344 motif was examined for the ability to interact with DAT. As confirmed in FIG. 1D, only GST fused to D2[IL3-2-5] (I311-Q344) (SEQ ID NO:1), but not GST fused to D2[IL3-2-4] (E297-I311) (SEQ ID NO: 17) precipitated DAT from solubilized striatal extract, indicating the I311-Q344 is required to form D2-DAT coupling.

These experiments show that a polypeptide having an amino acid sequence comprising I311-Q344 of a D2 receptor can bind to DAT. Accordingly, a polypeptide having an amino acid sequence comprising I311-Q344 of a D2 receptor can be useful for disrupting D2-DAT coupling. Further, such a peptide can be useful for modulating dopaminergic neurotransmission. Further still, such a peptide may be useful for treating one or more diseases as described herein.

Example 2

DAT Fragments that Bind to D2 Receptor from Rat Striatal Tissue

To locate the interacting site on DAT in D2-DAT coupling, GST-fusion proteins encoding the amino terminus (NT) and the carboxyl terminus (CT) of DAT were prepared: (GST fused to DAT[NT]:M1-D68 (SEQ ID NO:6); GST fused to DAT[CT]:L583-V620 (SEQ ID NO: 18) were used in affinity purification assay (FIG. 1E). These results reveal that the sequence encoded by the DAT[NT] facilitates the interaction with D2 receptors since only the GST fused DAT[NT] (SEQ ID NO:6), but not GST fused DAT[CT] (SEQ ID NO:18) (or GST alone), was able to pull-down D2 receptors. Further experiments show that GST fused DAT[NT1] (11-P26) (SEQ ID NO:7), but not the GST fused DAT[NT2] (A16-T43) (SEQ ID NO:9) or GST fused DAT[NT3] (K35-D68) (SEQ ID NO: 10), can successfully pull-down D2 receptors from solubilized rat striatum (FIG. 1F).

Therefore, the DAT[NT1] (M1-P26) (SEQ ID NO:7) region of DAT and D2[IL3-2-5] (I131-Q344) region (SEQ ID NO:1) of the D2 receptor are responsible for mediating the interaction between these two proteins. The amino acid sequence of DAT[NT1] is MSKSKCSVGLMSSVVAPAKEPNAVGP (SEQ ID NO:7).

While these results demonstrate the presence of the D2-DAT complex in rat striatal tissue, even further experiments were conducted to confirm that the D2-DAT complex is formed through a direct interaction between D2 and DAT. In vitro binding assay results demonstrated that [35S]-D2[IL3-2] (SEQ ID NO:3) hybridized with GST fused DAT[NT1] (SEQ ID NO:7) but not GST fused DAT[NT2] (SEQ ID NO:9) or GST fused DAT[NT3] (SEQ ID NO:10), suggesting the possibility of a direct D2-DAT interaction (FIG. 1G). Furthermore, there is in vitro evidence that the D2-DAT direct interaction is dependent on sequences located at the very beginning of the amino-terminus of the DAT. As shown in the in vitro binding assay in FIG. 1H, the interaction between the [35S]-D2[IL3-2] (SEQ ID NO:3) and GST fused DAT[NT1] (SEQ ID NO:7) is disrupted by co-incubation with the purified DAT[NT1-1] (M1-V15) peptide (SEQ ID NO:2), but not the DAT[NT1-2] (A16-P26) peptide (SEQ ID NO: 11). Taken together, these data support the existence of direct protein-protein interaction occurring between the D2 receptor and DAT and further confirm the role of M1-V15 region (SEQ ID NO:2) of DAT in maintaining the DAT-D2 direct protein-protein interaction.

The amino acid sequence of DAT[NT1-1] is MSKSKCSVGLMSSVV (SEQ ID NO:2).

These experiments show that a polypeptide having an amino acid sequence comprising M1-V15 (SEQ ID NO:2) of DAT can bind to a D2 receptor. Accordingly, a polypeptide having an amino acid sequence comprising M1-V15 of DAT can be useful for disrupting D2-DAT coupling. Further such polypeptides may be useful for modulating dopaminergic neurotransmission. Further still, the polypeptides may be useful for treating a variety of diseases as described herein.

Example 3

Figure 2:
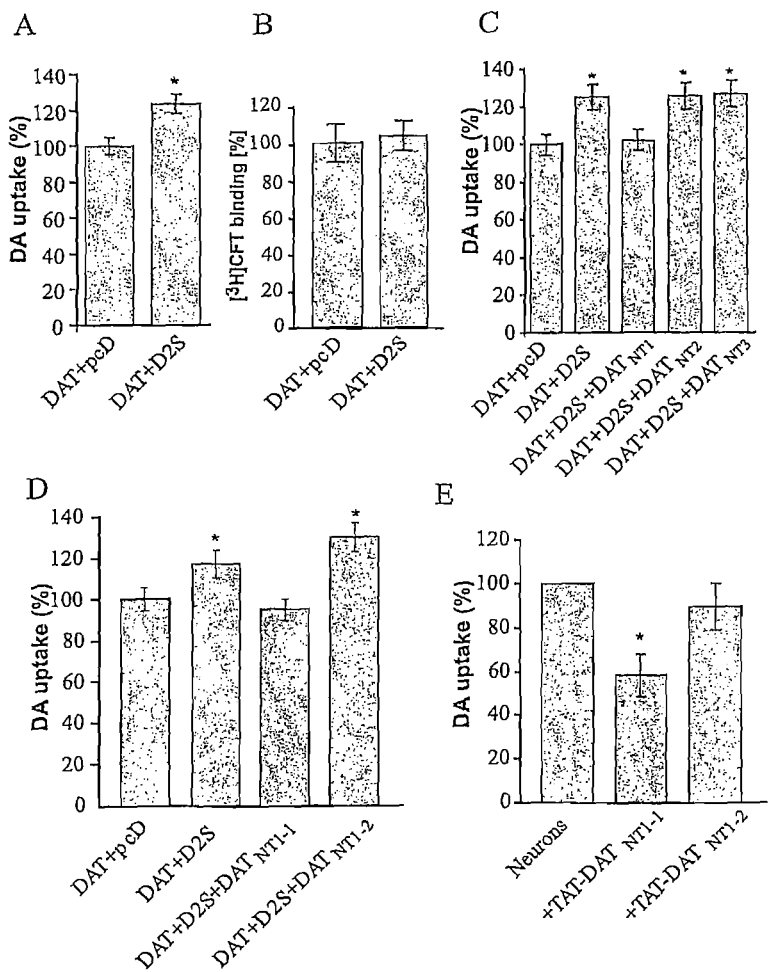
FIGS. 2A-E shows that coexpression of D2 receptor with DAT upregulates DA uptake in HEK-293 cells in accordance with a further embodiment of the present invention. (A) Co-transfecting D2 receptor and DAT cDNA into HEK-293 cells induced an increase in the Vmax for dopamine (DA) uptake accumulation by .about.25% (DAT/pcD: 1.22 pmol/$10^5$ cells/min; DAT/D2: 1.51 pmol/$10^5$ cells/min, t-test P<0.05, n=11) with no significant alteration in estimated Km values. The apparent enhancement of DA uptake was not due to a D2-induced increase in DAT expression levels since, as depicted in (B), the estimated whole-cell DAT levels, as indexed by the saturable binding of [3H]CFT, was not significantly different in DATexpressing cells or in cells co-transfected with the D2 receptor. (C) In HEK-293 cells, overexpression of DAT[NT1] (SEQ ID NO:7) mini-gene together with DAT and D2 blocked the increase of DAT uptake by D2 receptors while DAT[NT2] (SEQ ID NO: 9) and DAT[NT3] (SEQ ID NO:10) mini-genes have no effect. (D) The DAT[NT1-1] (SEQ ID NO:2) but not DAT[NT1-2] (SEQ ID NO: 11) mini-gene abolished D2-induced increase in DAT uptake in HEK-293 cells. (E) In rat midbrain primary cultures infected with DAT and D2 adenovirus, pre-incubation of TAT-DAT[NT1-1] peptide (SEQ ID NO:12), but not the TAT-DAT[NT1-2] peptide (SEQ ID NO:13), significantly decreased DA uptake. Data in C, D and E were analyzed by one-way ANOVA, post-hoc SNK test. *: P<0.05, n=3-5.

Coexpression of D2 Receptor with DAT Upregulates Dopamine (DA) Uptake in HEK-293 Cells The DAT is a major determinant of dopaminergic neurotransmission via its key role in terminating synaptic transmission and in regulating the concentration of DA available for binding to multiple post- and pre-synaptic dopamine D1 and D2 like receptors. To investigate the functional relevance of the D2-DAT interaction, changes in DAT activity upon coexpressing D2Short receptors (SEQ ID NO: 19) in HEK-293 cells was assessed. D2Short, instead of D2Long receptor (SEQ ID NO:20), was chosen based on previous studies that have shown that the D2Short receptor is the predominant presynaptic D2 receptor while D2Long is preferentially involved in postsynaptic signaling (18-20). As illustrated in FIG. 2A, the translocation velocity of cellular DAT-mediated DA uptake was significantly increased in HEK-293 cells co-transfected with D2 receptors relative to cells co-transfected with DAT and the mammalian expression vector pcD (DAT/pcD: 1.22±0.36 pmol/$10^5$ cells/min; DAT/D2: 1.51±0.31 pmol/$10^5$ cells/min; t-test P<0.05, n=11). Thus, the estimated Vmax for DAT-mediated [3H] DA uptake was enhanced by ~25% (FIG. 2A), with no significant change in the estimated Km of the DAT in D2 co-expressing cells (DAT/pcD: 1.96±0.31 µM; DAT/D2: 2.35±0.44 µM; t-test P=0.4256; n=11).

The enhancement of cellular DA uptake was not due to either a D2 induced increase in DAT expression as illustrated in FIG. 2B, in which whole cell Bmax estimates for the DAT, as indexed by the saturable binding of [3H] (2 beta-carbomethoxy-3 beta-(4-fluorophenyl)-tropane) ([3H]CFT), was not significantly different in control DAT expressing cells [52.3±5.5 fmol/$10^5$ cells] or in cells co-transfected with D2 [54.2±4 fmol/$10^5$ cells].

To further confirm that the observed D2 mediated enhancement of [3H]DA uptake by DAT is the product of DAT-D2 protein-protein complex formation, mini-genes encoding DAT sequences that are responsible for the interaction with D2 receptors, were expressed in HEK-293 cells co-expressing D2 and DAT. Mini-genes encoding DAT[NT1] (SEQ ID NO:7), DAT[NT2] (SEQ ID NO:9) and DAT[NT3] (SEQ ID NO: 10) were designed with overlapping regions of the DAT [NT] to minimize the chance of disrupting the D2 receptor binding motif. Co-expression of these mini-genes with DAT alone did not affect DAT activity (data not shown). However, co-expression of the mini-gene encoding DAT[NT1] (SEQ ID NO:7), but not DAT[NT2] (SEQ ID NO:9) or DAT[NT3] (SEQ ID NO:10), blocked the ability of D2 receptor to enhance DAT-mediated DA uptake when co-expressed with the DAT (FIG. 2C).

This example confirms that the DAT[NT1] (SEQ ID NO:7) region is responsible for the observed D2 modulation of DAT function, and is consistent with the data in FIGS. 1G, H showing the role of DAT[NT1] (SEQ ID NO:7) in the D2-DAT protein complex formation. In addition, expression of the mini-gene encoding DAT[NT1-1] (SEQ ID NO:2), which is able to disrupt the D2-DAT interaction, as shown in FIG. 1H, was also shown to significantly block the D2 mediated enhancement in DAT uptake of DA (FIG. 2D). This result confirms that amino acid residues M1-V15 (SEQ ID NO:2) of the DAT[NT] mediates both the direct protein-protein interaction between D2-DAT and facilitates the D2-dependent enhancement of DAT-mediated DA uptake.

Example 4

Coexpression of D2 Receptor with DAT Upregulates Dopamine (DA) Uptake in Neurons To examine the D2-DAT interaction in neuronal cells, primary rat midbrain neurons were utilized in parallel experiments to those described for HEK-293 cells in Example 3. Due to the low expression of both the DAT and D2 receptor and the heterogeneity of the cell population in primary midbrain neuronal cultures, primary midbrain neuronal cultures were infected with DAT and D2 receptor recombinant adenoviruses. To test the possible effect of the D2-DAT interaction on DAT uptake of DA, D2-DAT coupling was perturbed by introduction of the DAT[NT1-1] peptide (SEQ ID NO:2), which is responsible for the D2-DAT complex formation. DAT[NT1-1] (SEQ ID NO:2) and DAT[NT1-2] (SEQ ID NO:11) peptides were rendered cell-permeant by fusing each to the cell-membrane transduction domain of the human immunodeficiency virus type 1 (HIV-1) TAT protein (Tyr-Gly-Arg-Lys-Lys-Arg-Arg-Gln-Arg-Arg-Arg) (SEQ ID NO: 14) as previously reported (21). A fluorophore dansyl chloride was conjugated to the TAT-DAT[NT1-1] (SEQ ID NO:12) and TATDAT[NT1-2] (SEQ ID NO:13) peptides to verify the intracellular accumulation of TAT peptides by fluorescence microscopy (data not shown). Consistent with the data from HEK-293 cells, application of the TAT-DAT[NT1-1] peptide (SEQ ID NO:12) (10 µM for 30 minutes) in cultured neurons significantly reduced DAT-mediated DA uptake while the TAT-DAT[NT1-2] peptide (SEQ ID NO:13) did not produce any effects on the DAT uptake (FIG. 2E).

Example 5

Increase in DAT Plasma Membrane Localization Upon Coexpression of D2 Receptor

Figure 3:
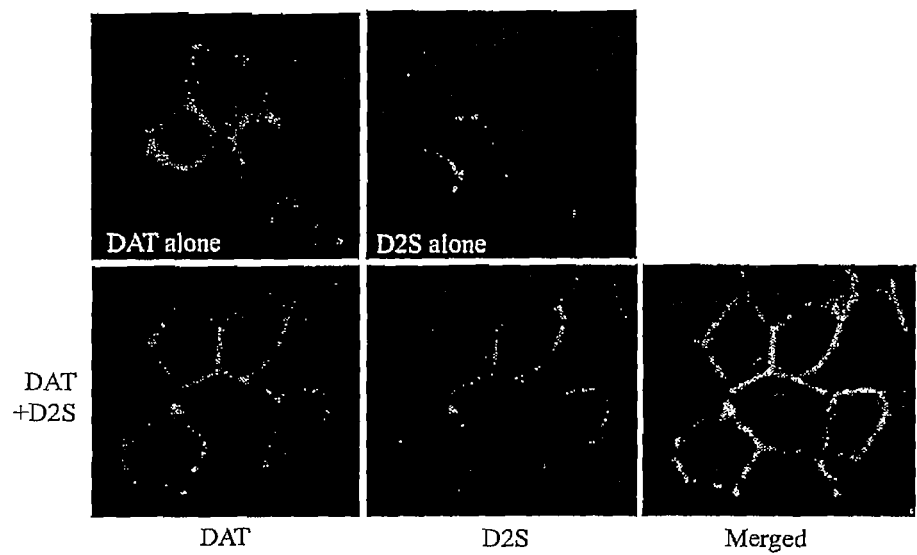
FIGS. 3A-C show an increase in DAT plasma membrane localization upon coexpression of D2 receptors in accordance with a further embodiment of the present invention. (A) Confocal microscopy of HEK-293 cells expressing D2 receptor, DAT or both were immunolabeled with DAT antibodies and/or D2 receptor antibodies. The DAT, in the absence of D2 receptor, exhibited dispersed immunolabelling throughout the cell (top panel). Co-expression of the D2 receptor and DAT reveals significant co-localization with a majority of the DAT localized at the cell surface (lower panel). (B) Quantification of DAT cell surface localization reveals that in HEK-293 cells co-expressing D2 receptor and DAT there is a ~20%, increase in DAT cell surface localization, compared to cells expressing only DAT, an effect which was blocked by the co-expression of DAT[NT1-1] (SEQ ID NO: 8) but not DAT [NT1-2] (SEQ ID NO: 11) mini-gene (one way ANOVA, post hoc SNK test, P<0.01, n=6). (C) Midbrain neuronal cultures incubated with TAT-DAT[NT1-1] peptide (SEQ ID NO:12, but not the TAT-DAT[NT1-2] peptide (SEQ ID NO:13) reveal a decrease (−10%) in DAT cell surface localization (one way ANOVA, post hoc SNK test, P<0.05, n=3).
Figure 3:
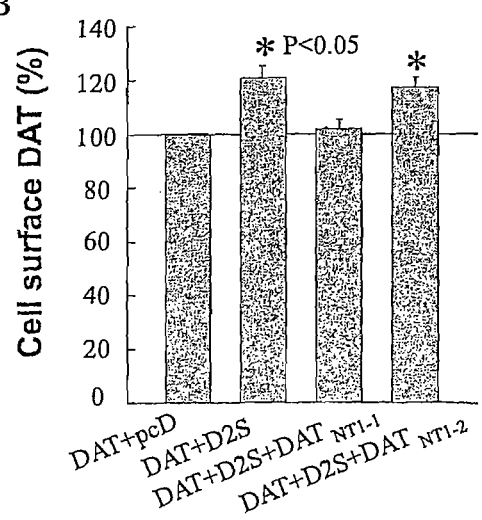
Figure 3:
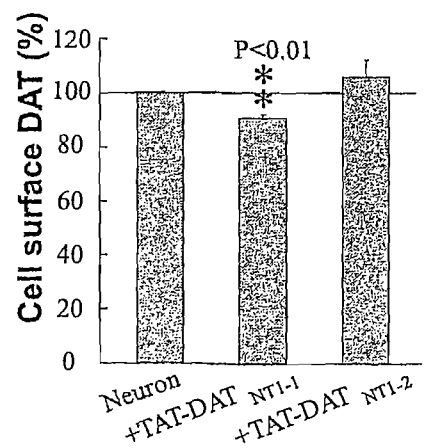

Previous work has suggested that the primary mechanism whereby the uptake velocity of the presynaptic DAT is decreased is through the rapid internalization of cell surface DAT into various intracellular compartments (22, 23). The observed enhancement of DA uptake by the coexpression with D2, which is independent of agonist stimulation and is not associated with increase in DAT protein levels, suggests the possibility that the observed augmentation of DAT function may result from the recruitment of an intracellular pool of DAT to the plasma membrane. FIG. 3A depicts confocal images and co-localization patterns of D2 and DAT when expressed in HEK-293 cells. Confocal immunofluorescent microscopy of HEK-293 cells expressing the DAT or D2 alone (top panel) indicates that the DAT is expressed quite diffusely throughout the cell. Upon co-expression with D2 receptors, however, the widespread diffuse intracellular distribution of DAT is substantially diminished (FIG. 3A, bottom panel) and instead DAT immunoreactivity is located primarily on the cell surface. Quantification of cell surface DAT, using cell-ELISA assays, revealed a ~21% increase in DAT plasma membrane localization by co-expression of D2 receptors (n=12, P<0.05) (FIG. 3B). Furthermore, this process could be blocked by over-expression of the DAT[NT1-1] (SEQ ID NO:2), but not DAT[NT1-2] (SEQ ID NO: 11) mini-genes, indicating that the enhanced DAT-mediated DA uptake may be a result of increased DAT plasma membrane expression. Similar data was also obtained in cultured midbrain neurons with the use of TAT-DAT[NT1-1] (SEQ ID NO: 12), and TAT-DAT[NT1-2] (SEQ ID NO:13) (FIG. 3C).

Example 6

Characterization of D2-DAT Interaction in Post-Mortem Brain in Human Patients

Agents that increase synaptic DA concentration (e.g. by amphetamine) have been previously shown to induce psychotic symptoms resembling schizophrenia, suggesting an impaired DA function may play a role in the pathology of schizophrenia (24, 25). In the context of the present inventor's finding that DAT mediated DA uptake can be up-regulated via direct protein-protein coupling with D2 receptors, disruption of D2-DAT interaction was predicted to lead to a hyper-dopaminergic state, due to decreased DAT function. To test this hypothesis, schizophrenia post-mortem brain tissue was examined for impairment of D2-DAT interaction using a co-immunoprecipitation assay.

60 post-mortem brain striatum samples were obtained from the Stanley Foundation, which includes 15 samples from each of the four groups: control, no schizophrenia, bipolar and severe depression. The four groups were matched by age, sex, race, postmortem interval, pH, side of brain, and mRNA quality by the Stanley Foundation brain bank. The coimmunoprecipitation experiments were carried out in a double-blind manner. The same amount of protein from each sample was incubated with anti-D2 receptor antibody and A/G agarose. The precipitated proteins were divided equally into two groups before being subjected to SDS-PAGE and immunoblotted with either DAT antibody or D2 antibody. Each Western blot includes 3 samples from each group and the intensity of each protein band was quantified by densitometry (software: AIS from Imaging Research Inc). Each sample is presented as the percent mean of three control samples on the same blot.

Figure 4:
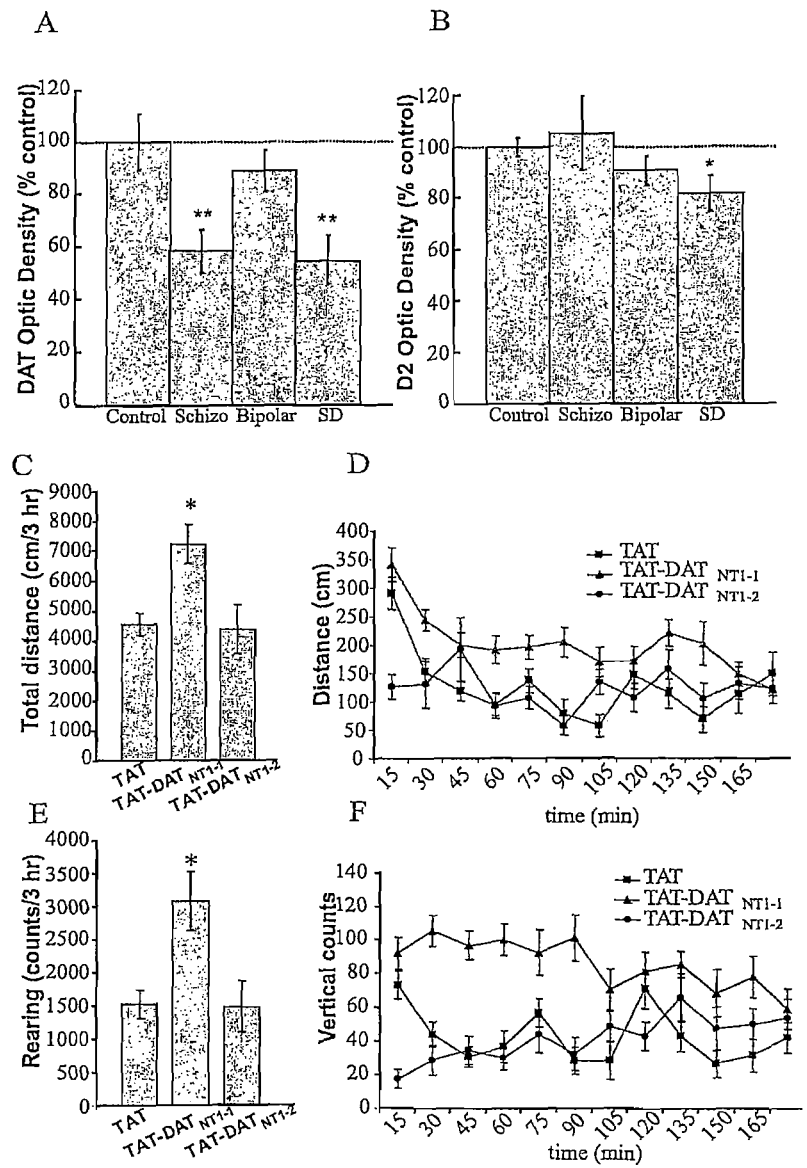
FIGS. 4A-F shows a characterization of D2-DAT interaction in post-mortem brain and physiological effect of disrupting D2-DAT coupling in accordance with a further embodiment of the present invention. Striatal post-mortem brain samples (control, schizophrenia, bipolar and severe depression [SD]; 15 samples in each group), obtained from the Stanley Foundation, were incubated with anti-D2 receptor antibodies for coimmunoprecipitation experiments. Precipitated proteins were subject to SDS-PAGE; immunoblotted with either DAT antibody (A) or D2 antibody (B). (A) Co-immunoprecipitation of DAT by the D2 antibody is significantly decreased in both schizophrenia and severe depression brains compared to controls. (B) The level of immunoprecipitated D2 receptor was not significantly altered in schizophrenia brain samples. However, the level of immunoprecipitated D2 receptors was decreased (−20%) in severe depression brain samples. Data were analyzed by one-way ANOVA followed by post-hoc SNK tests (P<0.05, n=15). (C-F) The TAT-DAT[NT1-1] peptide (SEQ ID NO: 12) (3 nM/g, 0.3 mL, IP), significantly increases locomotor activity compared to TAT (SEQ ID NO: 14) or TAT-DAT[NT1-2] peptides (SEQ ID NO: 13). Panels (C) and (D) show distance traveled (cm); panels (E) and (F) show vertical activity as a measure of rearing. Measures shown in (C) and (E) are the mean±SEM total counts over the 3 h test period. Panels (D) and (F) illustrate the time course of effects of TAT-DAT[NT1-1] (SEQ ID NO: 12). One way ANOVA, followed by post-hoc Student-Newman-Keuls test, showed significant treatment effects for distance traveled and rearing (*, P<0.01 TAT (SEQ ID NO: 14) vs TAT-DAT[NT1-1] (SEQ ID NO:12).

The coimmunoprecipitation of DAT by the D2 receptor antibody is significantly decreased in schizophrenia post-mortem brain samples compared to control brains (FIG. 4A). The levels of directly immunoprecipitated D2 receptors were not significantly different between the four groups (FIG. 4B). These results indicate that the D2-DAT interaction is perturbed in schizophrenia. In addition, a significant decrease (~40%) in D2-DAT co-immunoprecipitation was also observed in severe depression, but the levels of directly immunoprecipitated D2 receptors were also decreased (~20%), suggesting the observed decrease in D2-DAT coimmunoprecipitation was, partially, due to decreased levels of D2 receptors.

Most of the schizophrenia patients had been under antipsychotic treatment. However, despite many of the bipolar samples coming from patients that have also been treated with antipsychotics, no significant disruption in the D2-DAT interaction was observed. Therefore, the observed D2-DAT deficit seen in schizophrenia may be a primary aspect of schizophrenia pathophysiology, unrelated to the use of D2 antagonists.

Example 7

Physiological Effects of Disrupting D2-DAT Coupling in Mice

Previous studies have shown the DAT knock-out mice display significant spontaneous hyperlocomotion, reproduce several features of the amphetamine animal model of schizophrenia, are hyperactive, stereotypic, and show significant deficits in sensimotor gating and spatial cognitive function (26-29).

Since an impaired D2-DAT interaction would be expected to lead to decreased DAT mediated DA, which in turn would be expected to potentiate locomotor activity, mice treated with TAT-DAT[NT1-1] peptides (SEQ ID NO:12) to interfere with the D2-DAT interaction were examined for locomotor activity. One consequence of elevated dopaminergic transmission is behavioral activation (26-28).

Previous studies have shown that systemically injected TAT peptide penetrates the blood-brain barrier 1 hour after IP injection (21, 30). In the present work, injection of purified TAT-DAT[NT1-1] (SEQ ID NO:12) (3 mM/g, 0.3 mL, IP), but not the TAT-DAT[NT1-2] peptide (SEQ ID NO:13), significantly blocked the D2-DAT protein-protein interaction as illustrated in the co-immunoprecipitation results (data not shown). Consistent with the finding that TAT-DAT[NT1-1] (SEQ ID NO: 12) abolished the enhancement of DAT uptake induced by the co-expression of D2 receptors (FIG. 2E), TAT-DAT[NT1-1] (SEQ ID NO: 12) increased distance traveled and rearing (P<0.01) compared to treatment with TAT peptide (SEQ ID NO:14) or TATDAT[NT1-2] (SEQ ID NO:13) (FIGS. 4C-F). The observed increase in distance traveled and rearing is reminiscent of the DAT knockout mice (26).

Example 8

Agonist Stimulation of D2 Receptor Inhibits DAT-Mediated DA Uptake Through a Gi-Protein Dependent Pathway DA receptors exert their physiological functions upon agonist stimulation and thus the modulation of DAT uptake by activation of D2 was tested. In HEK-293 cells co-expressing D2 and DAT, activation of D2 receptors using 10 mM quinpirole significantly decrease DAT-mediated DA uptake by ~45% ($p<0.01$, n=3), an effect blocked by pre-incubating the cells with pertussis toxin (PTX) (150-200 ng/ml) (FIG. 7A), which uncouples the receptors from Gi/o protein, suggesting the involvement of Gi-dependent pathway. The effect of PTX to functionally block the ability of the D2 receptor to inhibit cAMP accumulation was confirmed in parallel experiment on cells co-expressing D2 with DAT (data not shown). In addition, quinpirole had no effect on DAT mediated DA uptake in cells co-transfected DAT with pcD (data not shown).

Example 9

Over-Expression of the Mini-Gene Expressing DATNT1-2 (SEQ ID NO:11) Abolishes D2 Receptor Agonist Mediated Inhibitory Effect on DAT-Mediated DA Uptake The third intracellular loop of the D2 receptor, which is responsible for coupling to Gi proteins, also mediates the interaction with the DAT. Thus, the relationship between the two pathways through which D2 regulates DAT-mediated DA uptake was tested. To examine whether the observed inhibitory effect on DAT-mediated DA uptake upon the activation of D2 receptors is dependent on the D2-DAT direct protein-protein interaction, DAT-mediated DA uptake was measured with or without D2 activation in HEK-293 cells co-transfected D2 receptor/DAT with the mini-gene expressing TAT-DAT[NT1-1] (SEQ ID NO:12) or TAT-DAT[NT1-2] (SEQ ID NO: 13) respectively. It was found that the inhibition of DAT uptake by D2 activation was abolished by over-expressing the mini-gene encoding TAT-DAT[NT1-2], but not the minigene encoding TAT-DAT[NT1-1] (FIGS. 7E,F), suggesting that the observed inhibitory effect on DAT-mediated DA uptake upon the activation of D2 receptors is independent on the physical coupling between the D2 receptor and DAT.

Example 10

Figure 7:
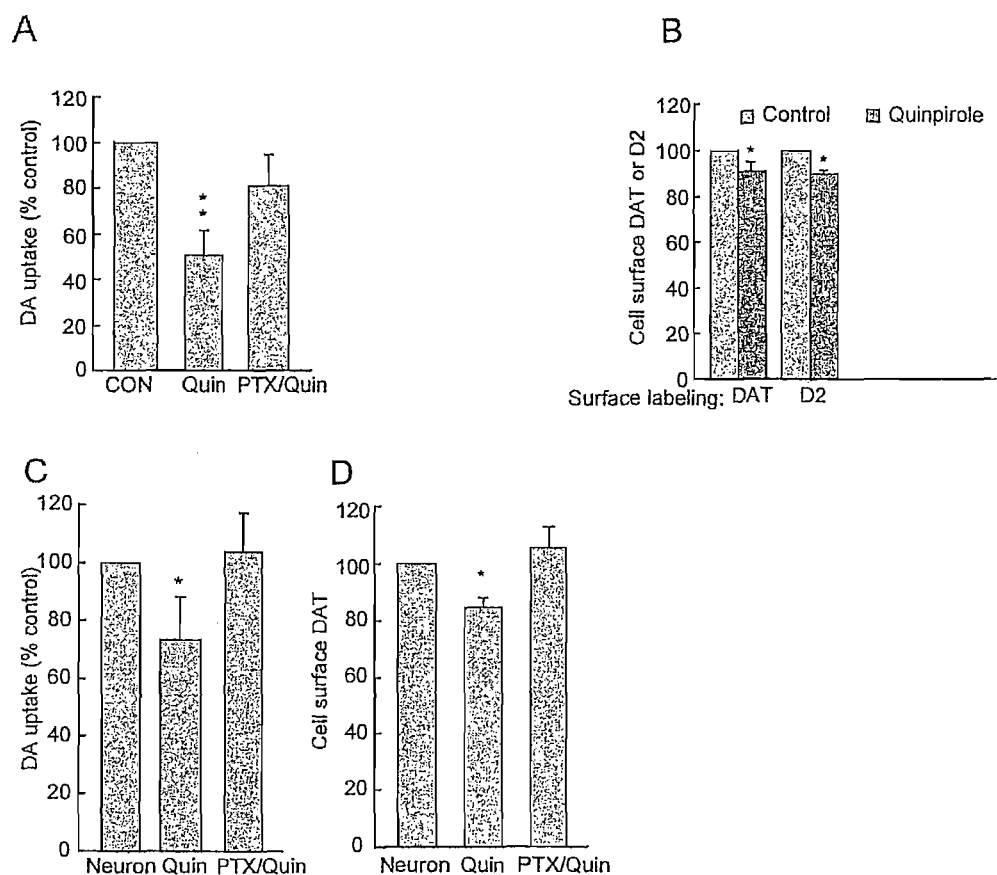
FIGS. 7A-F shows experimental results of dopamine uptake as a function treatment conditions (A), cell surface DAT or dopamine receptor D2 as a function of treatment conditions (B), DAT mediated dopamine uptake and DAT membrane expression in cultured midbrain neurons as a function of treatment conditions (C, D), and D2 receptor agonist mediated inhibitory effects on DAT mediated-DA uptake as a function of treatment conditions (E,F).
Figure 7E:
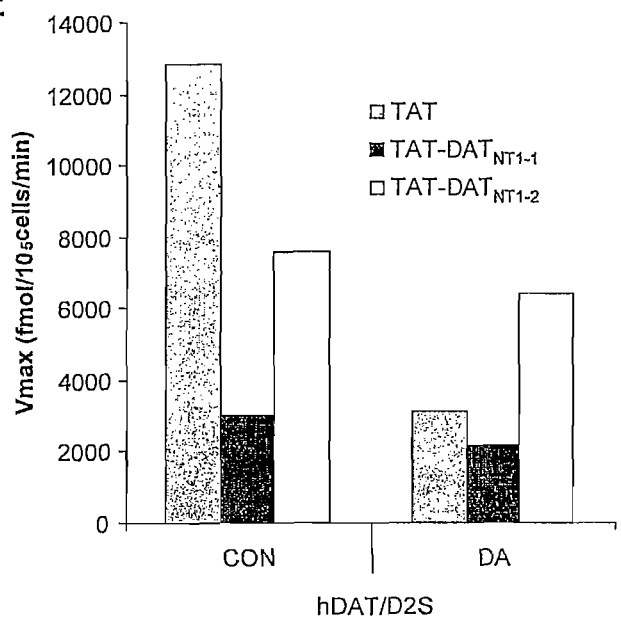
Figure 7F:
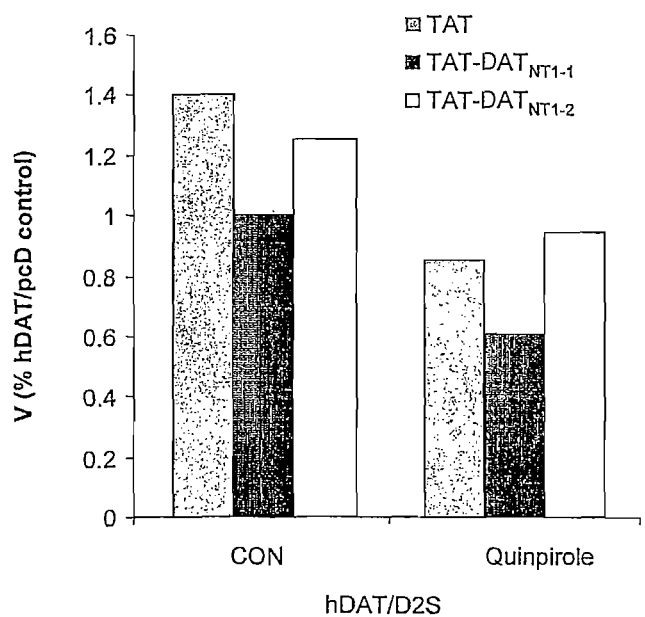

Activation of D2 Receptors Inhibits DAT-Mediated DA Uptake Through D2-DAT Co-Internalization As a member of the GPCR family, D2 receptors are subject to highly regulated mechanisms of internalization following agonist stimulation (Pierce and Lefkowitz, 2001). Previous studies have also suggested that the primary mechanism whereby DAT uptake velocity is decreased is through the rapid internalization of cell surface DAT into various intracellular compartments (Daniels and Amara, 1999; Melikian and Buckley, 1999). Without wishing to be bound by theory or limiting in any manner, given that D2 receptors directly couple to DAT in an agonist independent manner, it was predicted that the observed inhibition of DAT-mediated DA uptake upon agonist stimulation of D2 receptors is the consequence of D2-DAT protein complex co-internalization. As the cell-ELISA assays results show in FIG. 7B, activation of D2 receptors significantly decreased both D2 and DAT membrane expression. Similarly, inhibition of DAT-mediated DA uptake and DAT membrane expression by the activation of D2 receptor can be blocked by PTX in cultured midbrain neurons infected with both D2 and DAT adenoviruses (FIGS. 7C, D).

Example 11

Figure 8:
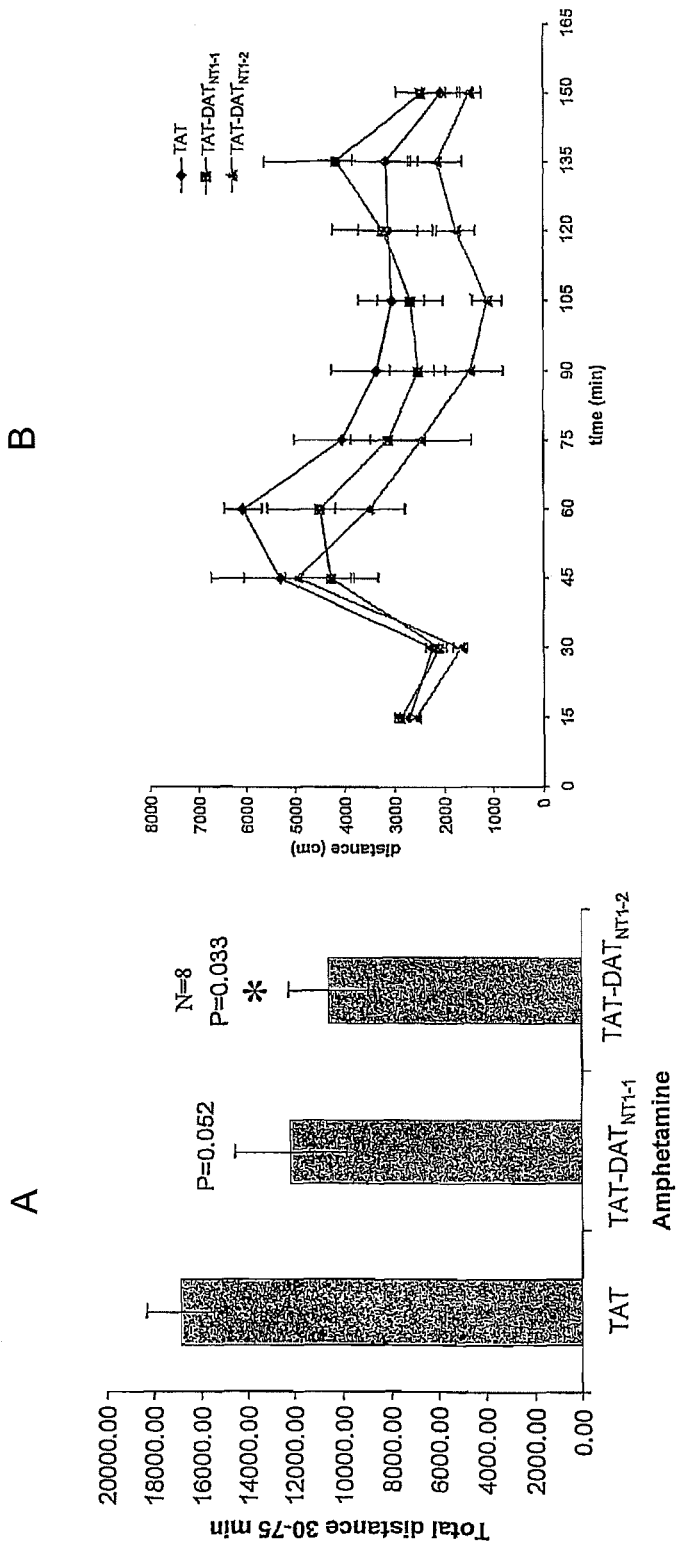
FIGS. 8A and B shows experimental results of total distance as a function of agent administered (A) and distance as a function of time for various agents administered (B) as described in the Examples.

TAT-DATNT1-2 (SEQ ID NO: 13) Injection Blocked the Amphetamine-Induced Hyper-Locomotor Activity The results presented herein provide evidence that the D2-DAT interaction facilitates D2 receptor activation mediated decrease in DAT activity—an effect mimicked by the DA agonist amphetamine. The strong psychomotor effect of amphetamine can be attributed to the release and accumulation of DA. An ability to mitigate this accumulation of synaptic DA may have profound consequences on drug addiction. It was found that the TAT-DATNT1-2 (SEQ ID NO:13) comprising A16-P26 peptide injection (ip injection, 3 nmol/g) can reduce the behavioural effects of amphetamine and potentially inhibit the development of drug addiction upon chronic administration (FIGS. 8A, B). Accordingly, agents comprising DATNT1-2 (SEQ ID NO:11), for example, but not limited to TAT-DATNT1-2 (SEQ ID NO:13) may be used to reduce the behavioral effects of amphetamine addiction.

It is also contemplated that agents comprising DATNT1-2 (SEQ ID NO: 11) may be employed in treating any disease or condition that would benefit from decreasing dopaminergic neurotransmission including, but not limited to schizophrenia and Tourette's syndrome.

In an embodiment of the present invention which is not meant to be limiting in any manner, there is provided a polypeptide of between about 7 and about 110 amino acids, for example, but not limited to 7, 8, 9, 10, 11, 12, 13, 14, 15, 16, 17, 18, 19, 20 or more amino acids and that comprise an amino acid sequence that is at between about 80% and about 100% identical, for example 80%, 85%, 90%, 95%, 96%, 97%, 98%, 99% or 100% identical to the sequence of DAT [NT1-2] (SEQ ID NO: 11). The present invention also contemplates polypeptides defined as having a range of amino acids as provided by any two of the values listed above or herein. Further, the present invention contemplates polypeptides defined as having a range of identities as determined by any two of the values listed above or herein.

In some embodiments, the disclosure provides theory and speculation on the mechanism of biological processes. The present invention is not meant to be bound by theory or speculation and the same should not be used to limit the invention in any way.

All citations are hereby incorporated by reference.

The present invention has been described with regard to one or more embodiments. However, it will be apparent to persons skilled in the art that a number of variations and modifications can be made without departing from the scope of the invention as defined in the claims.

REFERENCES

1. R. A. Wise, Nat Rev Neurosci 5, 483-94 (June 2004).
2. J. A. Girault, P. Greengard, Arch Neurol 61, 641-4 (May, 2004).
3. J. D. Berke, S. E. Hyman, Neuron 25, 515-32 (March, 2000).
4. J. Lotharius, P. Brundin, Nat Rev Neurosci 3, 932-42 (December, 2002).
5. M. Laruelle, L. S. Kegeles, A. Abi-Dargham, Ann NY Acad Sci 1003, 138-58 (November, 2003).
6. A. Breier et al., Proc Natl Acad Sci USA 94, 2569-74 (Mar. 18, 1997).
7. M. Laruelle et al., Proc Natl Acad Sci USA 93, 9235-40 (Aug. 20, 1996).
8. W. A. Cass, G. A. Gerhardt, Neurosci Lett 176, 259-63 (Aug. 1, 1994).
9. S. R. Jones et al., Nat Neurosci 2, 649-55 (July, 1999).
10. R. D. Mayfield, N. R. Zahniser, Mol Pharmacol 59, 113-21 (January, 2001).
11. S. M. Meiergerd, T. A. Patterson, J. O, Schenk, J Neurochem 61, 764-7 (August, 1993).
12. F. Liu et al., Nature 403, 274-80 (Jan. 20, 2000).
13. F. J. Lee et al., Cell 111, 219-30 (Oct. 18, 2002).
14. F. J. Lee, F. Liu, Z. B. Pristupa, H. B. Niznik, Faseb J 15, 916-26 (April, 2001).
15. A. M. Cameiro et al., J Neurosci 22, 7045-54 (Aug. 15, 2002).
16. G. E. Tones et al., Neuron 30, 121-34 (April 2001).
17. K. H. Lee, M. Y. Kim, D. H. Kim, Y. S. Lee, Neurochem Res 29, 1405-9 (July, 2004).
18. Z. U. Khan, L. Mrzljak, A. Gutierrez, A. de la Calle, P. S. Goldman-Rakic, Proc Natl Acad Sci USA 95, 7731-6 (Jun. 23, 1998).
19. D. Centonze et al., Neuropsychopharmacology 27, 723-6 (November, 2002).
20. N. Lindgren et al., Proc Natl Acad Sci USA 100, 4305-9 (Apr. 1, 2003).
21. M. Aarts et al., Science 298, 846-50 (Oct. 25, 2002).
22. H. E. Melikian, K. M. Buckley, J Neurosci 19, 7699-710 (Sep. 15, 1999).
23. G. M. Daniels, S. G. Amara, J Biol Chem 274, 35794-801 (Dec. 10, 1999).
24. M. Raiteri, A. Bertollini, F. Angelini, G. Levi, Eur J Pharmacol 34, 189-95 (November, 1975).
25. D. Sulzer et al., J Neurosci 15, 4102-8 (May, 1995).
26. B. Giros, M. Jaber, S. R. Jones, R. M. Wightman, M. G. Caron, Nature 379, 606-12 (Feb. 15, 1996).
27. R. R. Gainetdinov, S. R. Jones, M. G. Caron, Biol Psychiatry 46, 303-11 (Aug. 1, 1999).
28. R. J. Ralph, M. P. Paulus, F. Fumagalli, M. G. Caron, M. A. Geyer, J Neurosci 21, 305-13 (Jan. 1, 2001).
29. S. R. Jones, R. R. Gainetdinov, R. M. Wightman, M. G. Caron, J Neurosci 18, 1979-86 (Mar. 15, 1998).
30. S. R. Schwarze, A. Ho, A. Vocero-Akbani, S. F. Dowdy, Science 285, 1569-72 (Sep. 3, 1999).
31. M. E. Thase et al., J. Clin Psychiatry. 2005 66(8):974-81.
32. E. Coleman. Ann Intern Med. 2005. Sep. 6; 143(5):380-385.
33. R. T. Brown et al., Pediatrics 2005 115(6):749-757.
34. Hornykiewicz, Mov. Disor. 2002 May 17(3):501-508.
35. D. Banerjee, et al, Sleep Med. Rev. 2004 October; 8(5): 339-354.
36. P. Seeman and T. Lee, Science 1975 Jun. 20; 188(4194): 1217-9.
37. F. J. Jimenez-Jimenez and P. J. Garcia-Ruiz, 2001; 61(15): 2207-20.
38. J. M. Wilson et al., Annals of Neurology 40:428-439 (1996).
39. J. M. Wilson et al., Nature Medicine 2:699-703, 1996.

The invention claimed is:

1. An isolated polypeptide consisting of the amino acid sequence of SEQ ID NO: 1, 3 or 4.

2. The isolated polypeptide of claim 1 having the ability to disrupt D2 receptor-dopamine transporter (D2-DAT) coupling in a mammal.

3. The isolated polypeptide of claim 1, consisting of the amino acid sequence of SEQ ID NO:3.

4. The isolated polypeptide of claim 1 consisting of the amino acid sequence of SEQ ID NO: 1.

5. The isolated polypeptide of claim 1 consisting of the amino acid sequence of SEQ ID NO:4.

6. The isolated polypeptide of claim 1 is further fused to a protein transduction domain, wherein the protein transduction domain is the amino acid sequence of SEQ ID NO:14.

7. A method for increasing dopaminergic neurotransmission in a mammal in need of such treatment comprising administering to the mammal a therapeutically effective amount of the isolated polypeptide according to claim 1.

8. A method for increasing dopaminergic neurotransmission in a mammal in need of such treatment comprising administering to the mammal a therapeutically effective amount of an isolated polypeptide according to claim 1, wherein the isolated polypeptide disrupts dopamine D2 receptor-dopamine transporter (D2-DAT) coupling in the mammal.

* * * * *